(12) United States Patent
Nakatsugawa et al.

(10) Patent No.: US 8,358,740 B2
(45) Date of Patent: Jan. 22, 2013

(54) RADIOGRAPHIC IMAGE CAPTURING SYSTEM

(75) Inventors: Haruyasu Nakatsugawa, Kanagawa (JP); Naoto Iwakiri, Kanagawa (JP); Naoyuki Nishino, Kanagawa (JP); Yasunori Ohta, Kanagawa (JP); Yutaka Yoshida, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 224 days.

(21) Appl. No.: 12/970,975

(22) Filed: Dec. 17, 2010

(65) Prior Publication Data

US 2011/0170669 A1 Jul. 14, 2011

(30) Foreign Application Priority Data

Jan. 8, 2010 (JP) ................................. 2010-003256

(51) Int. Cl.
*H05G 1/58* (2006.01)

(52) U.S. Cl. ......................................... 378/116; 378/41

(58) Field of Classification Search ................... 378/41, 378/115–117
See application file for complete search history.

(56) References Cited

U.S. PATENT DOCUMENTS 7,706,505 B2 * 4/2010 Tachikawa .................. 378/98.8
8,243,883 B2 * 8/2012 Omernick et al. ............ 378/116

FOREIGN PATENT DOCUMENTS

| JP | 2005-323673 A | 11/2005 |
| JP | 2009-136481 A | 6/2009 |
| JP | 2009-186439 A | 8/2009 |

* cited by examiner

*Primary Examiner* — Hoon Song
(74) *Attorney, Agent, or Firm* — SOLARIS Intellectual Property Group, PLLC

(57) ABSTRACT

A radiographic image capturing system includes a radiographic image capture device, a radiation irradiation device, and a control device. The radiographic image capture device is capable of wired and wireless communications, and is capable of fluoroscopic imaging in which radiographic images are successively captured at notified synchronization timings or at a predetermined frame rate. The radiation irradiation device irradiates radiation toward the radiographic image capture device during fluoroscopic imaging, with continuous irradiation or pulse irradiation. The control device includes a wireless communication unit, a wired communication unit, and a controller that, if communication with the radiographic image capture device is performed by the wireless communication unit, prohibits fluoroscopic imaging with pulse irradiation in which the synchronization timings are notified to the radiographic image capture device and radiation is irradiated from the radiation irradiation device in pulses matching the notified synchronization timings.

8 Claims, 16 Drawing Sheets

FIG. 13
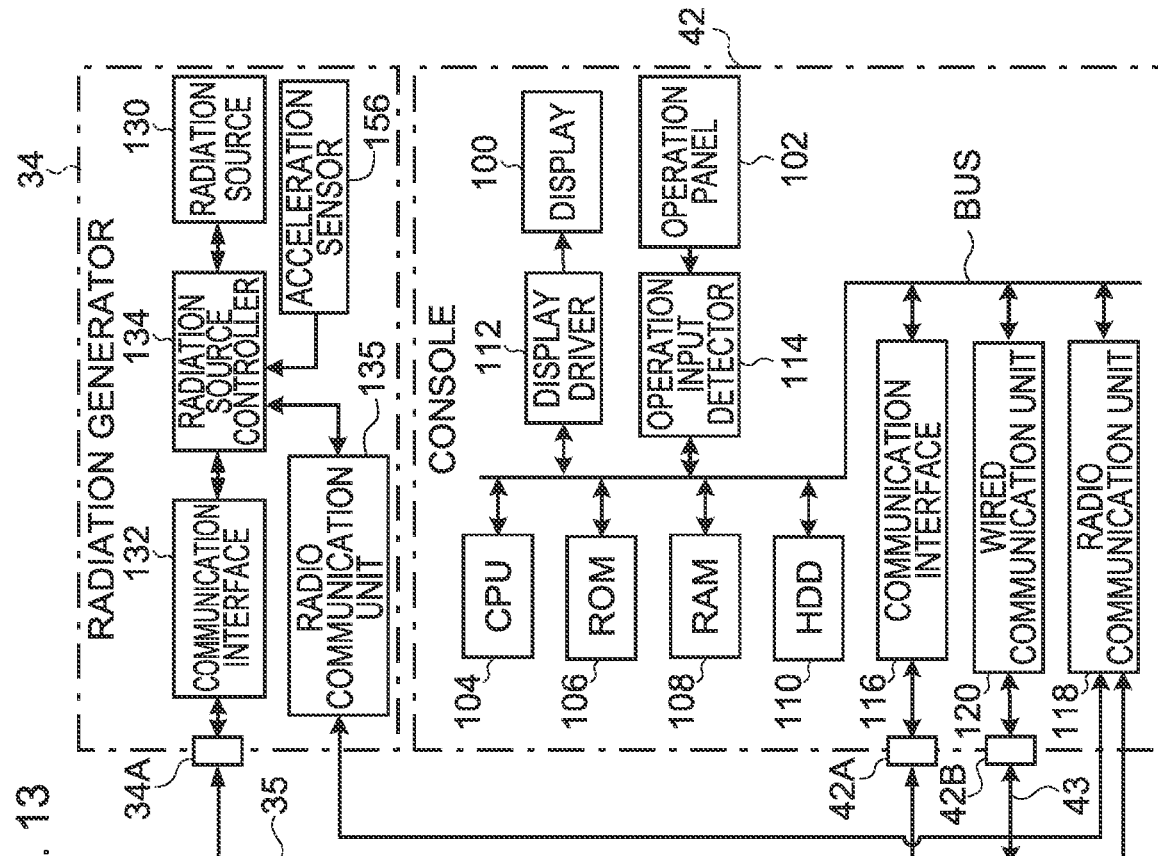
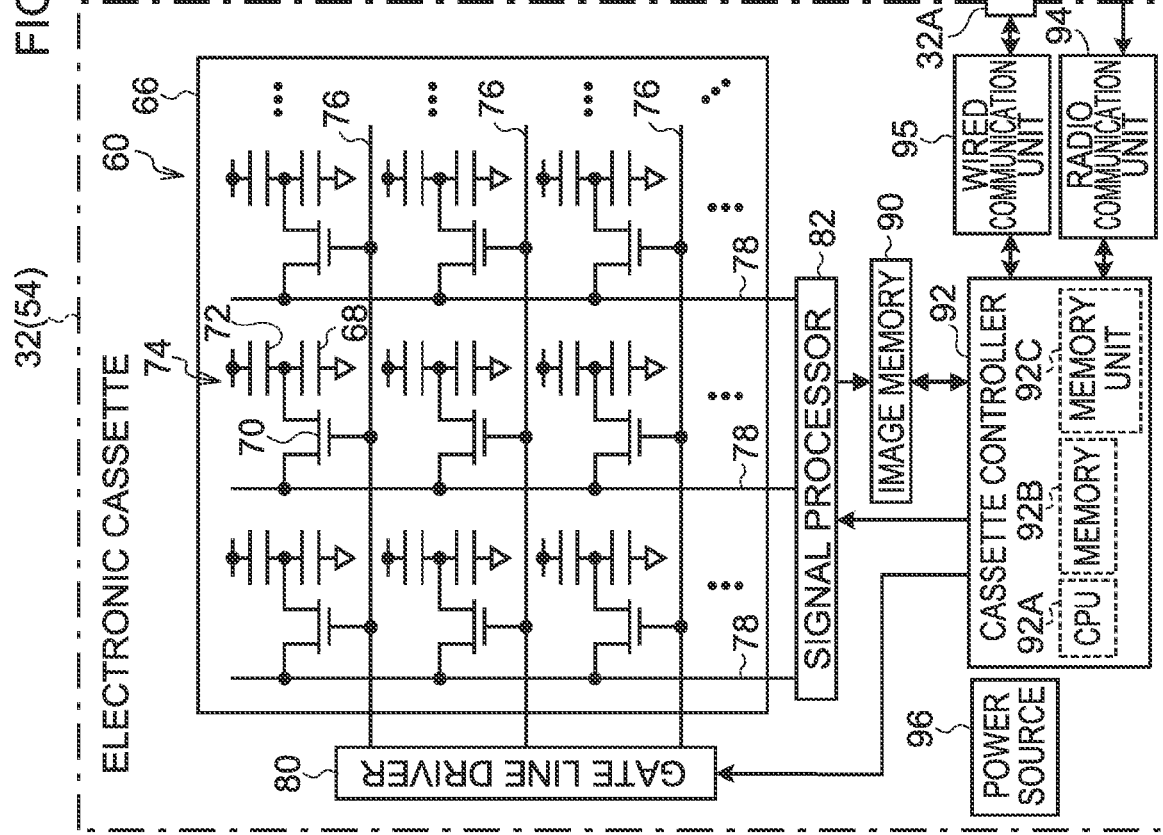

RADIOGRAPHIC IMAGE CAPTURING SYSTEM

CROSS-REFERENCE TO RELATED APPLICATION

This application claims priority under 35 USC 119 from Japanese Patent Application No. 2010-003256 filed on Jan. 8, 2010, the disclosure of which is incorporated by reference herein.

BACKGROUND OF THE INVENTION

1. Field of the Invention

The present invention relates to a radiographic image capturing system, and in particular, to a radiographic image capturing system that is capable of wired communication using a communication cable and wireless communication, and can carry out fluoroscopic imaging in which the capturing of radiographic images is carried out continuously at notified synchronization timings or at a predetermined frame rate.

2. Description of the Related Art

Radiation detectors such as flat panel detectors (FPDs), in which a radiation-sensitive layer is disposed on a thin film transistor (TFT) active matrix substrate and that can convert radiation directly into digital data have been put into practice in recent years. Portable radiographic image capturing devices (hereinafter also called "electronic cassettes"), that capture radiographic images expressed by irradiated radiation by using the radiation detector, are being put into practice. As compared with a radiographic image capturing device that uses a conventional X-ray film or imaging plate, a radiographic image capturing device that uses the radiation detector has the advantages that images can be confirmed immediately, and fluoroscopic imaging (video image capturing), in which the capturing of radiographic images is carried out continuously, also can be carried out. As methods of converting radiation at the radiation detector, there are an indirect conversion method that, after converting radiation into light at a scintillator, converts the light into charges at a semiconductor layer of photodiodes or the like, and a direct conversion method that converts radiation into charges at a semiconductor layer of amorphous selenium or the like, and the like. There exist various types of materials that can be used at the semiconductor layer in these respective methods.

As image capturing methods for fluoroscopic imaging, there are a method of capturing images at a predetermined frame rate while irradiating radiation continuously from a radiation source (continuous irradiation), and a method of, while irradiating radiation in the form of pulses synchronously with the frame rate (pulse irradiation), capturing images synchronously with the irradiation of the radiation. With pulse irradiation, the radiation can be irradiated for the time needed for imaging, and the amount of radiation that the patient is exposed to can be suppressed as compared with continuous irradiation, and there is therefore the advantage that the irradiated amount per unit time can be increased. However, with pulse irradiation, there is the need to synchronize the timing of irradiating the radiation from the radiation source and the timing of the image capturing at the radiation detector.

Japanese Patent Application Laid-Open (JP-A) No. 2009-136481 discloses a technique in which a switch for switching between continuous irradiation and pulse irradiation is provided. In imaging using C arm, when the C arm is rotated and positioning of the imaged region is carried out, the form of irradiation is switched to pulse irradiation by the switch. When capturing diagnostic images, the form of irradiation is switched to continuous irradiation by the switch, and image capturing is carried out.

JP-A No. 2009-186439 discloses, in a wireless X-ray fluoroscopic system that is physically divided into an exposure unit and a sensor unit, a technique of generating beacon signals at a period that is associated with the frame rate of image capturing, and wirelessly synchronizing the irradiation timing and the image capturing timing.

Electronic cassettes generally have better usability if communication thereof with a control device (known as a console) is wireless communication than wired communication using a communication cable.

For such cases, using the technology recited in JP-A No. 2009-186439 and generating a beacon signal with a period corresponding to a frame rate of image capture to synchronize irradiation timings with image capture timings has been considered.

However, if transmitting and synchronizing beacon signals by radio communication to synchronize irradiation timings with image capture timings is attempted, the synchronization is difficult because of communication delays and the like, and fluoroscopic images may not be captured reliably.

Radio communication between an electronic cassette and a control device has been described here, but the same applies in a case in which communication between a control device and a radiation irradiation device or between an electronic cassette and a radiation irradiation device is performed by radio communication and synchronization of irradiation timings with capture timings is performed by radio communication.

SUMMARY

The present invention has been made in consideration of the above, and provides a radiographic image capturing system capable of reliably capturing fluoroscopic images.

An aspect of the present invention is a radiographic image capturing system including: a radiographic image capture device that is capable of wired communication via a communication cable and of wireless communication, and that is capable of fluoroscopic imaging in which radiographic images are successively captured at notified synchronization timings or at a predetermined frame rate; a radiation irradiation device that irradiates radiation toward the radiographic image capture device during fluoroscopic imaging, with continuous irradiation or pulse irradiation; and a control device that includes a wireless communication unit that performs wireless communication with the radiographic image capture device, a wired communication unit that performs wired communication with the radiographic image capture device via the communication cable, and a controller that, in a case in which communication with the radiographic image capture device is performed by the wireless communication unit, prohibits fluoroscopic imaging with pulse irradiation in which the synchronization timings are notified to the radiographic image capture device and radiation is irradiated from the radiation irradiation device in pulses matching the notified synchronization timings.

Thus, according to the aspect described above, in a case in which communication between the control device and the radiographic image capture device is to be implemented by radio communication, fluoroscopic imaging is prohibited in which synchronization timings are notified to the radiographic image capture device and radiation is irradiated in pulses from the radiation irradiation device to match the synchronization timings. Thus, fluoroscopic images may be captured reliably.

In the present aspect, the control device may further include a storage unit that memorizes unsuitable condition data representing a condition under which fluoroscopic imaging with continuous irradiation is unsuitable, and the controller warns against or prohibits fluoroscopic imaging with continuous irradiation if the fluoroscopic imaging is to be carried out under the condition represented by the unsuitable condition data.

Thus, fluoroscopic imaging may be warned against or prohibited if the fluoroscopic imaging would be carried out in unsuitable conditions.

In the present aspect, a radiation amount per unit time that is irradiated by the radiation irradiation device may be smaller in the continuous irradiation than in the pulse irradiation.

Thus, exposure of a subject when radiation is being continuously irradiated may be restrained.

In the present aspect, the radiographic image capture device may includes a radiographic detector in which a plurality of pixels that generate charges when radiation is irradiated thereon and store the charges are arranged in two dimensions, the radiographic detector outputting the charges stored in the pixels as electronic signals; amplifiers that amplify the electronic signals output by the radiographic detector; and an image capture device controller that, in case in which the continuous irradiation is performed, performs at least one of: extending a storage period of the charges at the pixels to be longer than in the pulse irradiation; increasing a gain amount of the amplifiers to be higher than in the pulse irradiation; or image processing that combines a plurality of adjacent pixels as a single pixel.

Thus, even in a case in which fluoroscopic imaging is performed with continuous illumination and the illuminated radiation amount per unit time is reduced, excellent images may be obtained.

The present aspect may further include a detector that detects shaking of the radiation irradiation device, and the controller may initiate a warning if a shake amount of the radiation irradiation device detected by the detector during fluoroscopic imaging is at least a first shake threshold value, and may stop irradiation of the radiation from the radiation irradiation device if the shake amount is at least a second shake threshold value, which is larger than the first shake threshold value.

Thus, even if shake of the radiation irradiation device occurs, a warning may be given if the shake amount is greater than the first shake threshold, and irradiation of the radiation may be stopped if the shake amount is greater than the second shake threshold.

In the present aspect, the controller may initiate the warning and stop the irradiation of the radiation if the detector detects shaking of the radiation detection device during fluoroscopic imaging with continuous irradiation.

Thus, if shake of the radiation irradiation device is detected during fluoroscopic imaging in which radiation is continuously irradiated, a warning is given or irradiation of the radiation is stopped, depending on the shake amount.

Another aspect of the present invention is a radiographic image capturing system including: a radiation irradiation device that is capable of wired communication via a communication cable and of wireless communication, and that irradiates radiation during fluoroscopic imaging in which radiographic images are successively captured with continuous irradiation or with pulse irradiation synchronized with notified synchronization timings; and a control device that includes a wireless communication unit that performs wireless communication with the radiation irradiation device, a wired communication unit that performs wired communication with the radiation irradiation device via the communication cable, and a controller that, in a case in which communication with the radiation irradiation device is performed by the wireless communication unit, prohibits fluoroscopic imaging with pulse irradiation in which the synchronization timings are notified to the radiation irradiation device and radiation is irradiated from the radiation irradiation device in pulses matching the notified synchronization timings.

According to this aspect, in a case in which communication between the control device and the radiation irradiation device is to be implemented by radio communication, fluoroscopic imaging is prohibited in which synchronization timings are notified to the radiation irradiation device and radiation is irradiated in pulses from the radiation irradiation device to match the synchronization timings. Thus, fluoroscopic images may be captured reliably.

Still another aspect of the present invention is a radiographic image capturing system including: a radiation irradiation device that is capable of wired communication via a communication cable and of wireless communication, and that irradiates radiation during fluoroscopic imaging in which radiographic images are successively captured, with continuous irradiation or with pulse irradiation synchronized with notified synchronization timings; and a control device that includes a wireless communication unit that performs wireless communication with the radiation irradiation device, a wired communication unit that performs wired communication with the radiation irradiation device via the communication cable, an image capture unit that performs image capture at the synchronization timings or at a predetermined frame rate, and a controller that, in case in which communication with the radiation irradiation device is performed by the wireless communication unit, prohibits fluoroscopic imaging with pulse irradiation in which the synchronization timings are notified to the radiation irradiation device and image capture is performed by the image capture unit in pulses matching the synchronization timings.

According to this aspect, in a case in which communication between the radiation irradiation device and the control device is to be implemented by radio communication, fluoroscopic imaging is prohibited in which synchronization timings are notified to the control device and image capture is carried out by the imaging section to match the synchronization timings. Thus, fluoroscopic images may be captured reliably.

BRIEF DESCRIPTION OF THE DRAWINGS

Exemplary embodiments of the present invention will be described in detail based on the following figures, wherein:

FIG. 13 is a block diagram illustrating a configuration of principal elements of an electronic system of an imaging system relating to a second exemplary embodiment;

DETAILED DESCRIPTION

Exemplary embodiments of the present invention are described in detail hereinafter with reference to the drawings. Note that, here, description is given of examples of a case in which the present invention is applied to a radiology information system that is a system that all-inclusively manages information handled in the radiology department of a hospital.

First Exemplary Embodiment

Figure 1:
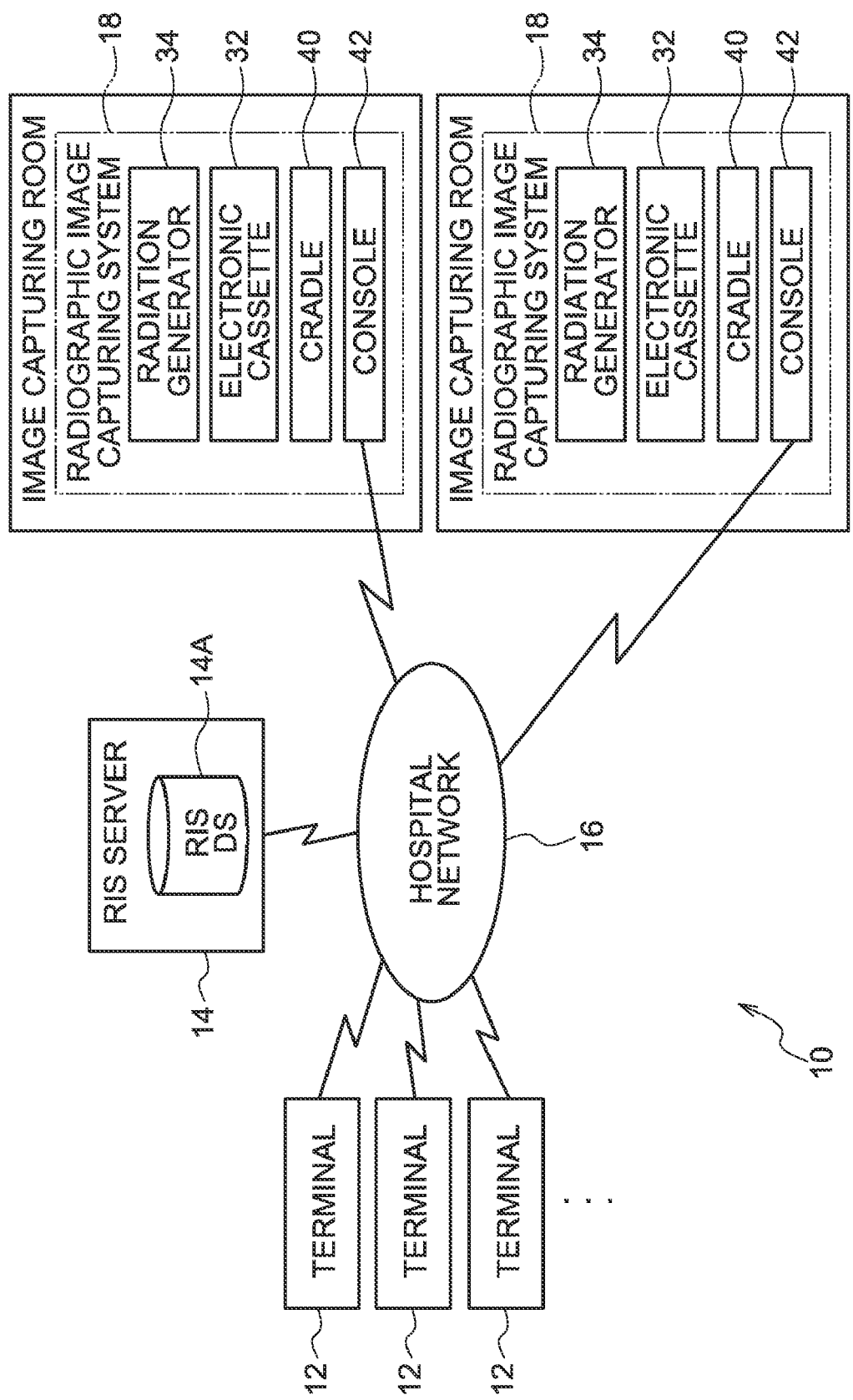
FIG. 1 is a block diagram illustrating a configuration of a radiology information system relating to an exemplary embodiment.

A configuration of a radiology information system 10 (which will be called "the RIS 10" below) of the present embodiment will be described in reference to FIG. 1.

The RIS 10 is a system for managing information such as medical service appointments and diagnostic records in a radiology department and configures part of a hospital information system (HIS).

The RIS 10 includes plural image capture request terminals 12 (which will be called "the terminals 12" below), a RIS server 14 and radiographic image capturing systems 18 (hereinafter, referred to as "capturing systems") installed in individual radiographic image capturing rooms (or operating rooms) in a hospital being connected to a hospital network 16 that is structured by a wired or wireless local area network (LAN). The RIS 10 serves as part of the HIS that is disposed in the same hospital, and an HIS server (not shown) that manages the entire HIS is also connected to the hospital network 16.

The terminals 12 are devices for doctors or a radiologic technologist to input/browse diagnostic information and facility reservations, and requests to capture radiographic images or image capture reservations are also performed from the terminals 12. Each of the terminals 12 is configured by a personal computer equipped with a display device, and the terminals 12 are connected by the hospital network 16 to the RIS server 14 so as to be capable of communicating with each other.

The RIS server 14 receives the image capture requests from the terminals 12, manages radiographic image capture schedules in the image capturing systems 18, and includes a database 14A.

The database 14A includes information relating to a patient, such as attribute information or data (name, sex, date of birth, age, blood type, weight, patient ID (identification) and the like) of the patient, medical history, consultation history, and radiographic images captured in the past.

The image capturing systems 18 capture radiographic images by operation of the doctors or radiologic technologists in response to an instruction from the RIS server 14. Each of the capturing systems 18 is equipped with a radiation generator 34 that irradiates a subject with radiation X (see also FIG. 3) from a radiation source 130 (see also FIG. 2) of a radiation amount corresponding to image capture conditions, an electronic cassette 32 that includes a radiation detector 60 (see also FIG. 3) that absorbs the radiation X that has been transmitted through an image capture area of the patient and generates charges, and generates image information representing radiographic image information (data) based on the generated charge amount, a cradle 40 that charges a battery built into the electronic cassette 32, and a console 42 that controls the electronic cassette 32, the radiation generator 34, and the cradle 40.

Figure 2:
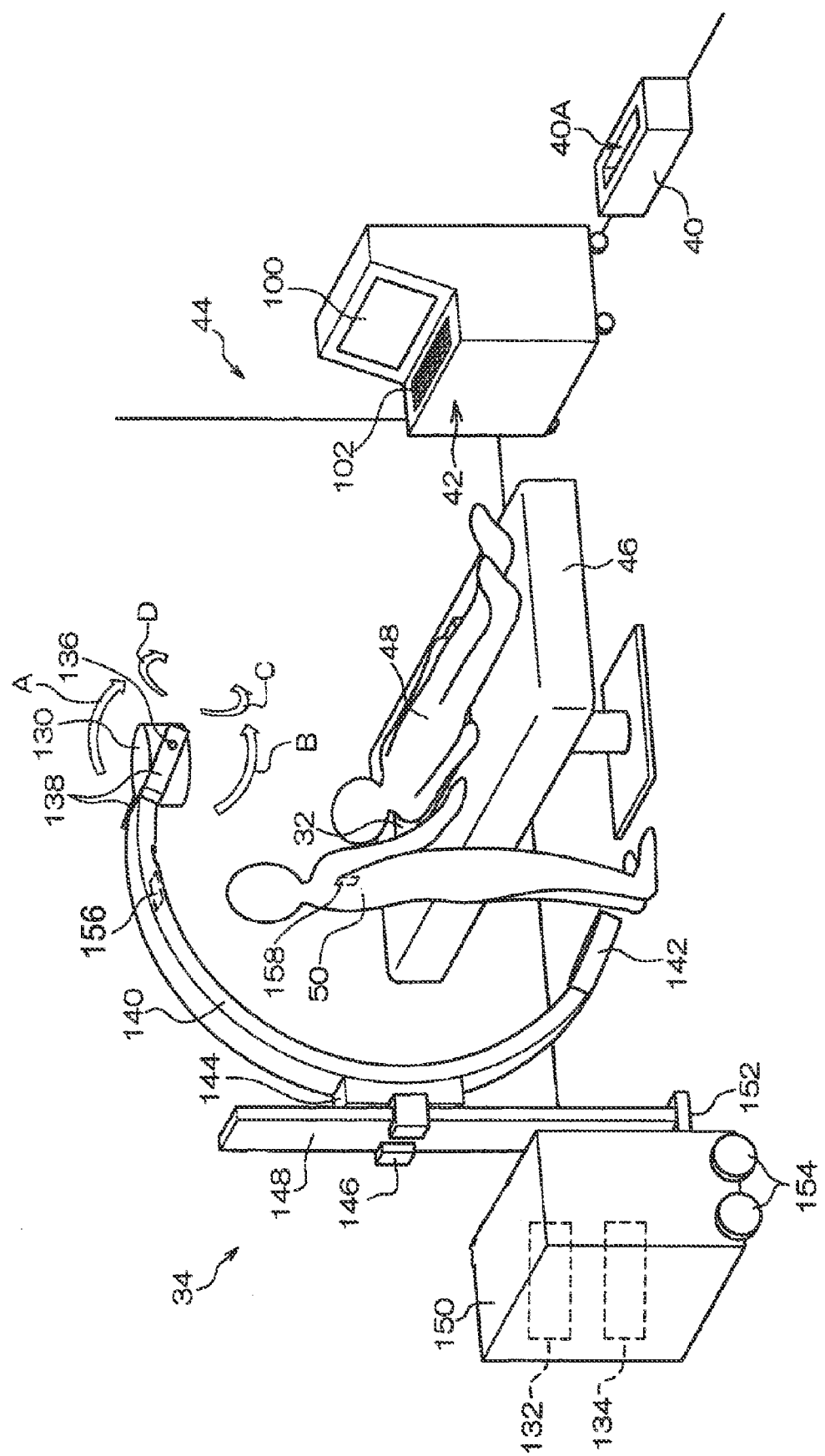
FIG. 2 is a perspective diagram illustrating an example of arrangements of devices in a radiographic image capturing room and a configuration of a radiation generator of the radiology information system relating to the exemplary embodiment.

FIG. 2 shows an example of the arrangements of the image capturing systems 18 in an radiographic image capturing room 44 and a configuration of the radiation generator 34 according to the present exemplary embodiment. In the image capturing system 18, the console 42 is mutually connected to the radiation generator 34 such that these devices transmit and receive various types of information (data) by wired communication, but in FIG. 2, the cables that interconnect these devices are omitted. Further, the electronic cassette 32 and the console 42 may transmit and receive various types of information (data) by radio communication or wired communication.

The radiation generator 34 relating to the present exemplary embodiment has a C arm 140. The radiation source 130 that emits radiation X is provided at one end of the C arm 140. An attachment structure 142, to and from which the electronic cassette 32 can be attached and removed, is provided at the other end of the C arm 140. Note that FIG. 2 shows a state in which the electronic cassette 32 is removed from the attachment structure 142 and is provided between a bed 46, that is provided at the substantially central portion of the radiographic image capturing room 44, and a subject (patient) 48 who is lying on the bed 46.

The radiation source 130 is provided at one end of the C arm 140 via a supporting shaft 136 and a pair of supporting plates 138. The radiation source 130 can be rotated in direction A and direction B in FIG. 2 around the supporting shaft 136, and can be rotated together with the supporting plates 138 in direction C and direction D in FIG. 2 around a tangent line of the arc of the C arm 140.

A C arm holding portion 144, that holds the C arm 140 such that the C arm 140 can rotate clockwise and counterclockwise in FIG. 2, is provided at a position that abuts the outer periphery of the cylindrical surface of the C arm 140. The C arm holding portion 144 is held, via a C arm holding portion 146, at a support 148 so as to freely move vertically. Further, the C arm holding portion 144 is supported so as to be able to rotate around a horizontal axis with respect to the C arm holding portion 146.

The radiation generator 34 has a main body 150 that incorporates therein a communication interface 132, a radiation source controller 134, and the like that are described below. The lower end of the support 148 is mounted to a support supporting section 152 that projects-out to the side from a vicinity of the lower end portion of the housing of the main body 150.

Wheels 154 are provided at the bottom portion of the main body 150, such that the radiation generator 34 can move within the hospital.

The cradle 40 and the console 42 are set in a vicinity of a wall in the radiographic image capturing room 44 relating to the present exemplary embodiment.

A housing portion 40A that can house the electronic cassette 32 is formed in the cradle 40.

When the electronic cassette 32 stands by, the electronic cassette 32 is housed in the housing portion 40A of the cradle 40 and the built-in battery is charged, and when a radiographic image is to be captured, the electronic cassette 32 is removed from the cradle 40 and disposed in the area of the patient 30 of which an image is to be captured, or mounted on the attachment structure 142 of the C arm 140 of the radiation generator 34.

The electronic cassette 32 is not limited to being used in the operating room 44 and can also be applied to medical screenings and rounds inside a hospital, for example.

Figure 3:
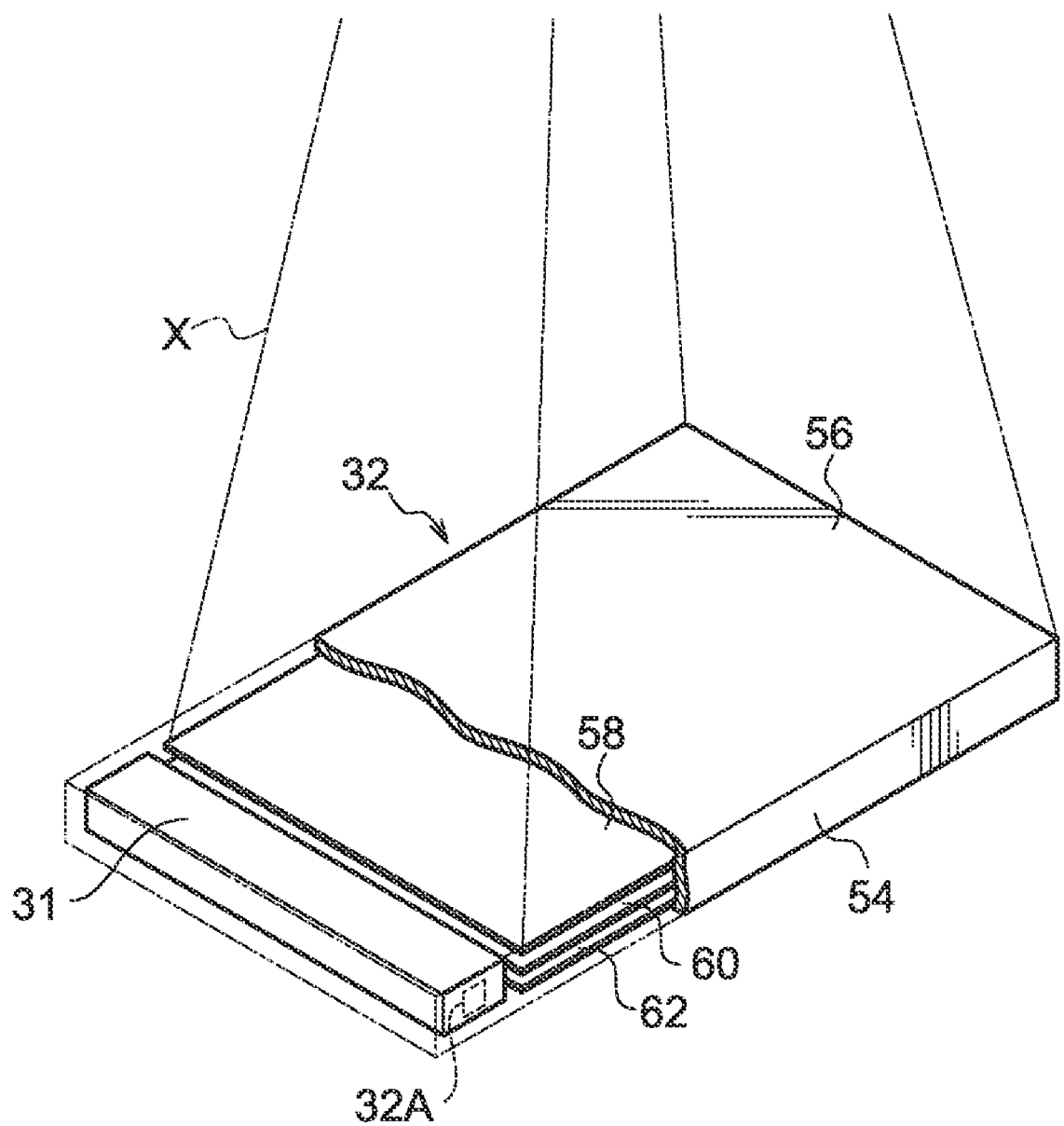
FIG. 3 is a cutaway perspective diagram illustrating an internal configuration of an electronic cassette relating to the exemplary embodiment.

FIG. 3 shows the internal configuration of the electronic cassette 32 pertaining to the exemplary embodiment.

As shown in FIG. 3, the electronic cassette 32 is equipped with a casing 54 formed by a material that allows the radiation X to be transmitted therethrough, and the electronic cassette 32 is configured to have a waterproof and hermetic structure. There is the fear that blood or another contaminant may adhere to the electronic cassette 32 in a case in which the electronic cassette 32 is used in an operating room or the like. Thus, the electronic cassette 32 is configured to have a waterproof and hermetic structure and is washed with an antiseptic as needed, so that one electronic cassette 32 can be used repeatedly.

Inside the casing 54, there are disposed, in order from an irradiated surface 56 of the casing 54 that is irradiated with the radiation X, a grid 58 that removes scattered radiation of the radiation X resulting from the patient, the radiation detector 60 that detects the radiation X that has been transmitted through the patient, and a lead plate 62 that absorbs back scattered radiation of the radiation X. The irradiated surface 56 of the casing 54 may also be configured by the grid 58. A connection terminal 32A for connecting a cable 43 is provided at a side of the casing 54.

A case 31 that houses electronic circuits including a microcomputer and a rechargeable secondary battery is disposed on one end side of the inside of the casing 54. The radiation detector 60 and the electronic circuits are actuated by power supplied from the secondary battery disposed in the case 31. A lead plate or the like may be disposed on the irradiated surface 56 side of the case 31 in order to avoid a situation where the various circuits housed inside the case 31 sustain damage in accompaniment with being irradiated with the radiation X.

In the present exemplary embodiment, the electronic cassette 32 is configured as a rectangular parallelepiped in which the irradiated surface 56 is formed in a rectangle shape, and the case 31 is disposed at one side in a longitudinal direction of the rectangular parallelepiped.

Figure 4:
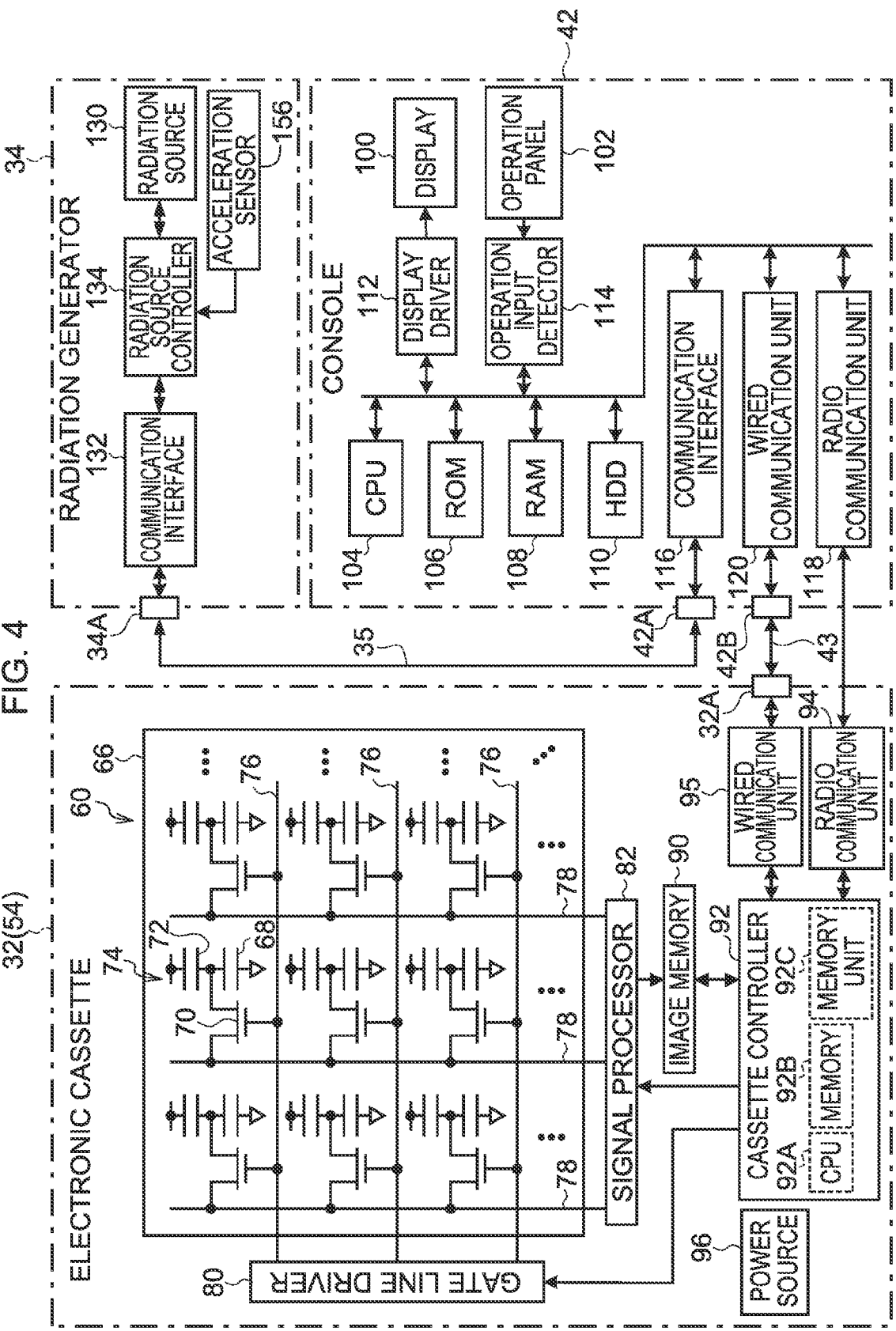
FIG. 4 is a block diagram illustrating a configuration of principal elements of an electronic system of an imaging system relating to a first exemplary embodiment.

FIG. 4 shows a block diagram showing the detailed configuration of the radiographic image capturing system 18.

A connection terminal 34A for performing communication with the console 42 is disposed in the radiation generator 34. A connection terminal 42A for performing communication with the radiation generator 34, a connection terminal 42B for performing communication with the electronic cassette 32 are disposed in the console 42. The connection terminal 34A of the radiation generator 34 and the connection terminal 42A of the console 42 are connected with a cable 35.

In a case in which the electronic cassette 32 performs wired communication, the cable 43 is connected to the connection terminal 32A and the electronic cassette 32 is connected to the console 42 via the cable 43.

The radiation detector 60 built into the electronic cassette 32 is configured by a photoelectric conversion layer that absorbs and converts the radiation X into electric charges being layered on a TFT active matrix substrate 66. The photoelectric conversion layer contains, for example, amorphous selenium (a-Se) whose main component (e.g., having a content percentage equal to or greater than 50%) is selenium, and when the photoelectric conversion layer is irradiated with the radiation X, the photoelectric conversion layer converts the radiation X which has been irradiated into electric charges by generating, inside itself, electric charges (electron-hole pairs) of an electric charge amount corresponding to the amount of the radiation X which has been irradiated. The radiation detector 60 may also, instead of a material that directly converts the radiation X into electric charges such as amorphous selenium, use a fluorescent material and a photoelectric conversion element (photodiode) to indirectly convert the radiation X into electric charges. As the phosphor material, gadolinium oxysulfide (GOS) and cesium iodide (CsI) are well known. In this case, conversion of the radiation X into light is performed by the fluorescent material, and conversion of the light into electric charges is performed by the photodiode of the photoelectric conversion element.

Further, on the TFT active matrix substrate 66, numerous pixels 74 (in FIG. 4, the photoelectric conversion layer corresponding to the individual pixels 74 is schematically shown as photoelectric converters 72) equipped with storage capacitors 68 that store the electric charges that have been generated by the photoelectric conversion layer and TFTs 70 for reading the electric charges that have been stored in the storage capacitors 68 are arranged in a matrix. The electric charges that have been generated in the photoelectric conversion layer by the irradiation of the electronic cassette 32 with the radiation X are stored in the storage capacitors 68 of the individual pixels 74. Thus, the image information that had been carried in the radiation X with which the electronic cassette 32 was irradiated is converted into electric charge information (an amount of electric charge) and is held in the radiation detector 60.

Further, on the TFT active matrix substrate 66, there are disposed plural gate lines 76, which extend in a constant direction (row direction) and are for switching ON and OFF the TFTs 70 of the individual pixels 74, and plural data lines 78, which extend in a direction (column direction) orthogonal to the gate lines 76 and are for reading the stored electric charges from the storage capacitors 68 via the TFTs 70 that have been switched ON. The individual gate lines 76 are connected to a gate line driver 80, and the individual data lines 78 are connected to a signal processor 82. When the electric charges are stored in the storage capacitors 68 of the individual pixels 74, the TFTs 70 of the individual pixels 74 are switched ON in order in row units by signals that are supplied via the gate lines 76 from the gate line driver 80. The electric charges that are stored in the storage capacitors 68 of the pixels 74 whose TFTs 70 have been switched ON are transmitted through the data lines 78 as electric charge signals and are input to the signal processor 82. Consequently, the electric charges that are stored in the storage capacitors 68 of the individual pixels 74 are read in order in row units.

Figure 5:
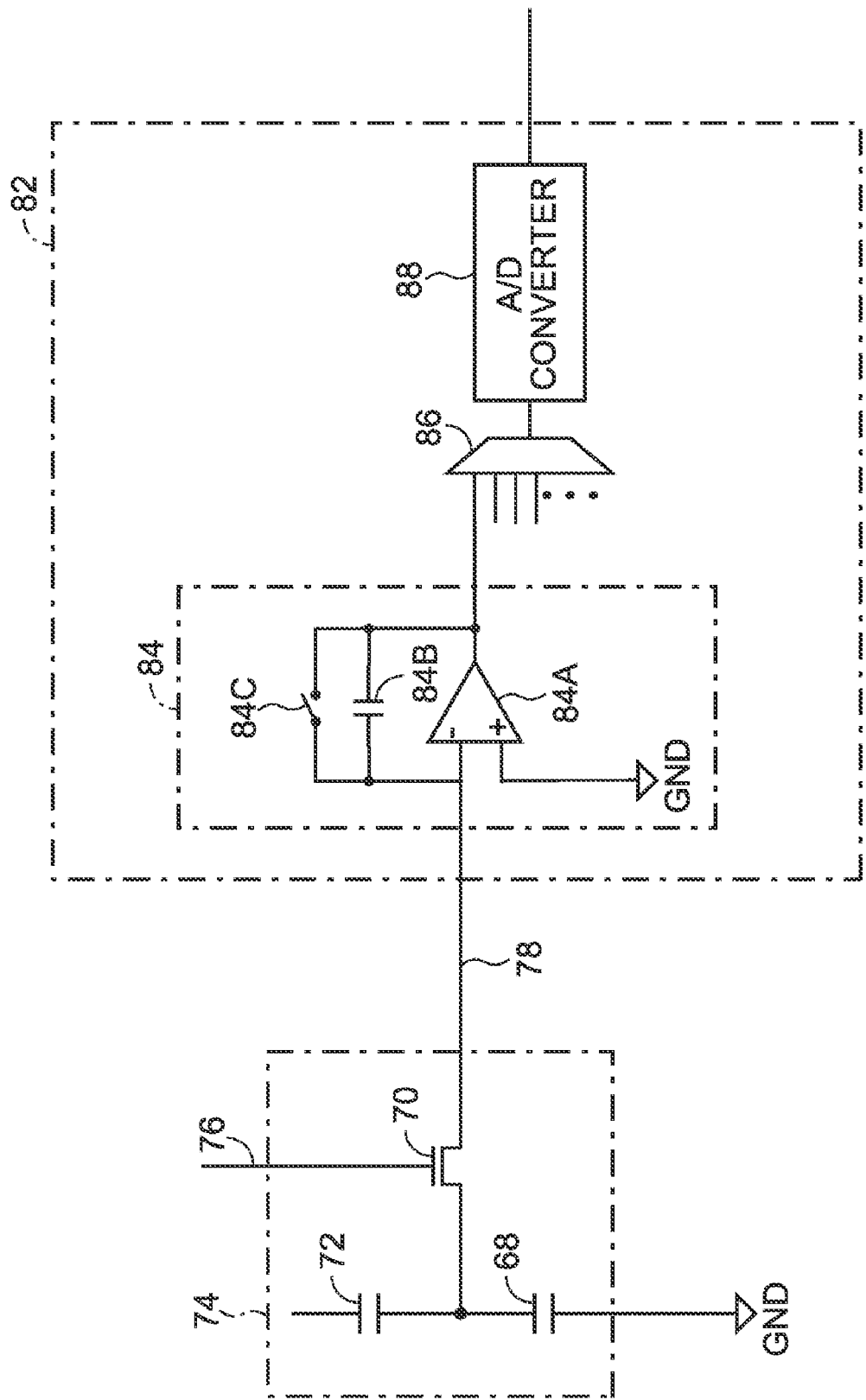
FIG. 5 is an equivalent circuit diagram concerning a single pixel portion of a radiation detector relating to the exemplary embodiment.

FIG. 5 shows an equivalent circuit diagram focusing on one pixel portion of the radiation detector 60 pertaining to the exemplary embodiment.

As shown in FIG. 5, a source of the TFT 70 is connected to the data line 78, and the data line 78 is connected to the signal processor 82. Further, a drain of the TFT 70 is connected to the storage capacitor 68 and to the photoelectric converter 72, and a gate of the TFT 70 is connected to the gate line 76.

The signal processor 82 is equipped with a sample/hold circuit 84 for each of the individual data lines 78. The electric charge signals that have been transmitted through the individual data lines 78 are held in the sample/hold circuits 84. The sample/hold circuit 84 includes an operational amplifier (op-amp) 84A and a capacitor 84B and converts the electric charge signal into an analog voltage. Further, a switch 84C, which serves as a reset circuit that causes both electrodes of the capacitor 84B to short to cause the electric charge stored in the capacitor 84B to be discharged as a result of the switch 84C being switched ON, is disposed in the sample/hold circuit 84. The gain of the operational amplifier 84A can be adjusted by control of a cassette controller 92 which will be described later.

A multiplexer 86 and an analog/digital (A/D) converter 88 are connected in this order at an output side of the sample/hold circuits 84. The electric charge signals held in the individual sample/hold circuits 84 are converted into analog voltages, and the analog voltages are input in order (serially) to the multiplexer 86 and converted into digital image data by the A/D converter 88.

An image memory 90 is connected to the signal processor 82 (see FIG. 4). The image data that have been output from the A/D converter 88 of the signal processor 82 are stored in order in the image memory 90. The image memory 90 has a storage capacity that is capable of storing a predetermined number of frames' worth of image data representing a radiographic image, and each time imaging of a radiographic image is performed, image data obtained by the imaging is sequentially stored in the image memory 90.

The image memory 90 is connected to the cassette controller 92 that controls operation of the entire electronic cassette 32. The cassette controller 92 is realized by a microcomputer, and includes a central processing unit (CPU) 92A, a memory 92B including a read only memory (ROM) and a random access memory (RAM), and an non-volatile storage section 92C that may formed of a hard disk drive (HDD), flash memory or the like.

A radio communication unit 94 and a wired communication unit 95 are connected to the cassette controller 92. The radio communication unit 94 is adapted to a wireless local area network (LAN) specification represented by for example IEEE (Institute of Electrical and Electronics Engineers) 802.11a/b/g and controls the transmission of various types of information between the electronic cassette 32 and an external device by radio communication. The wired communication unit 95 is connected to the connection terminal 32A and performs the transmission of various types of information between the electronic cassette 32 and the console via the connection terminal 32A and the cable 43. The cassette controller 92 can perform communication with the console 42 via the radio communication unit 94 or the wired communication unit 95, and transmits various types of information to and receives various types of information from the console 42 via the radio communication unit 94 or the wired communication unit 95. The cassette controller 92 stores exposure conditions received via the radio communication unit 94 or the wired communication unit 95, which will be described later, and starts reading out of charges based on the exposure conditions.

A power source 96 is provided in the electronic cassette 32, and the various circuits and elements mentioned above (such as the gate line driver 80, the signal processor 82, the image memory 90, the radio communication unit 94, the wired communication unit 95, and the microcomputer that functions as the cassette controller 92) are actuated by power supplied from the power source 96. The power source 96 has a built-in battery (a rechargeable secondary battery) so as to not impair the portability of the electronic cassette 32, and the power source 96 supplies power to the various circuits and elements from the charged battery. In FIG. 4, wirings connecting the various circuits and elements and the power source 96 are omitted.

The console 42 is configured as a server computer and is equipped with a display 100, which displays operation menus and radiographic images that have been captured, and an operation panel 102, which includes plural keys and by which various types of information and operation instructions are input.

Further, the console 42 pertaining to the exemplary embodiment is equipped with a central processing unit (CPU) 104 that controls operation of the entire device, a read-only memory (ROM) 106 in which various programs including a control program are stored beforehand, a random-access memory (RAM) 108 that temporarily stores various types of data, a hard disk drive (HDD) 110 that stores and maintains various types of data, a display driver 112 that controls the display of various types of information on the display 100, an operation input detector 114 that detects states of operation with respect to the operation panel 102. The console 42 further includes a communication interface 116 that is connected to the connection terminal 42A and transmits various types of information to and receives various types of information from the radiation generator 34 via the connection terminal 42A and the cable 35 such as later-described exposure conditions, a radio communication unit 118 that transmits and receives various types of information such as the exposure conditions between the electronic cassette 32, and a wired communication unit 120 that is connected to the connection terminal 42B and transmits and receives various types of information such as image data between the electronic cassette 32 via the connection terminal 42B and the cable 43.

The CPU 104, the ROM 106, the RAM 108, the HDD 110, the display driver 112, the operation input detector 114, the communication interface 116, the radio communication unit 118, and the wired communication unit 120 are interconnected via a system bus BUS. Consequently, the CPU 104 can access the ROM 106, the RAM 108 and the HDD 110, can control the display of various types of information on the display 100 via the display driver 112, can control the transmission of various types of information to and the reception of various types of information from the radiation generator 34 via the communication interface 116, can control the transmission of various types of information to and the reception of various types of information from the electronic cassette 32 via the radio communication unit 118, and can control the transmission of various types of information to and the reception of various types of information from the electronic cassette 32 via the wired communication unit 120. Further, the CPU 104 can grasp states of operation by a user with respect to the operation panel 102 via the operation input detector 114.

The radiation generator 34 is equipped with the radiation source 130 that outputs the radiation X, a communication interface 132 that transmits various types of information to and receives various types of information from the console 42 such as exposure conditions, and a radiation source controller 134 that controls the radiation source 130 on the basis of received exposure conditions.

The radiation source controller 134 is also realized by a microcomputer, stores the received exposure conditions, and causes the radiation source 130 to irradiate the radiation X on the basis of the exposure conditions.

An acceleration sensor 156 is provided at the radiation generator 34 relating to the present exemplary embodiment in a vicinity of the position where the radiation source 130 is set at the C arm 140 as shown in FIG. 2, in order to prevent failures in the capturing of radiographic images caused by some object contacting or colliding with the radiation source 130. In the present exemplary embodiment, the acceleration sensor 156 is a sensor that senses the way of application of velocity with respect to three axial directions that are the vertical direction, the left-right direction and the front-back direction. The acceleration sensor 156 may be any type provided that it can detect acceleration, and may be, for example, a piezoresistance type sensor or an electrostatic capacity type sensor.

As shown in FIG. 4, the acceleration sensor 156 is connected to the radiation source controller 134. Signals, that are output from the acceleration sensor 156 and express the accelerations in the three axial directions, are input to the radiation source controller 134. The radiation source controller 134 transmits the acceleration information (data), that is input from the acceleration sensor 156 and expresses the accelerations in the three axial directions, to the console 42 via the communication interface 132.

Next, overall operation of the capturing system 18 pertaining to the exemplary embodiment will be described.

The electronic cassette 32 and the console 42 pertaining to the exemplary embodiment perform wired communication in a case in which they are interconnected by the cable 43 and perform radio communication in a case in which they are not interconnected by the cable 43.

The capturing system 18 of the present exemplary embodiment is configured to be capable of selecting a capturing mode from still image capturing that performs capturing one by one, or fluoroscopic imaging that performs capturing continuously. Further, the capturing system 18 is configured to be capable of selecting, in the fluoroscopic imaging, continuous irradiation in which radiation is continuously irradiated from the radiation source 130 or pulse irradiation in which radiation is irradiated in pulsed form from the radiation source 130 in synchronization with the frame rate of the capturing, during the capturing.

One of the terminals 12 (see FIG. 1) receives an image capture request from doctors or radiologic technologists. In the image capture request, there are designated a patient to be captured, the area of the patient to be captured, the capturing more, and optionally the tube voltage, the tube current, the irradiation time, and the total radiation amount.

The terminal 12 notifies the RIS server 14 of the content of the received image capture request. The RIS server 14 stores, in the database 14A, the content of the image capture request which has been notified by the terminals 12.

The console 42 accesses the RIS 14 to acquire the content of the image capture request and the attribute data of a patient to be captured from the RIS server 14 and display the content of the image capture request and the attribute data of the patient on the display 100 (see FIG. 4).

An operator initiates capture of a radiographic image on the basis of the content of the image capture request displayed on the display 100.

For example, as shown in FIG. 2, in a case in which capture of a radiographic image of an affected area of the subject 48 lying on the bed 46 is to be performed, the operator disposes the electronic cassette 32 between the bed 46 and the affected area of the subject 48 for the area to be imaged without connecting the cable 43 to the electronic cassette 32 and the console 42 in case of using radio communication, or after connecting the electronic cassette 32 and the console 42 with the cable 43 in case of using wired communication.

Figure 6:
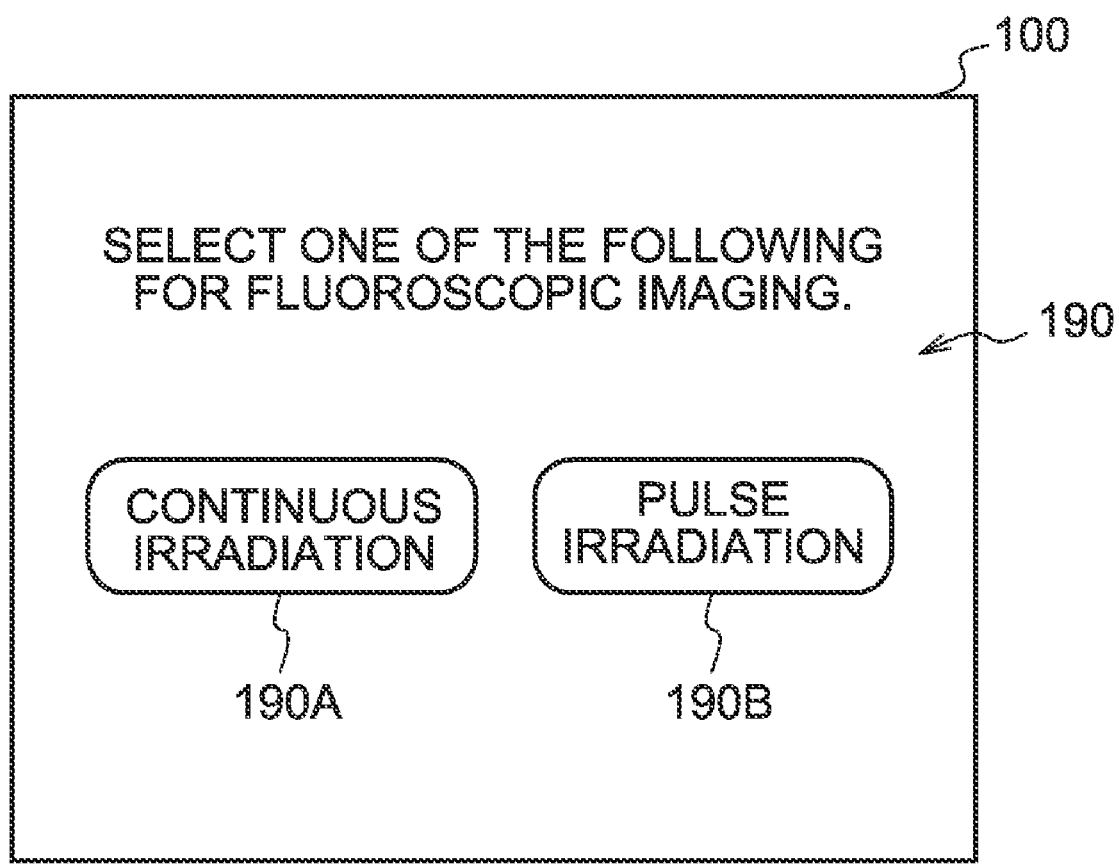
FIG. 6 is a schematic diagram illustrating an example of an instruction screen relating to the exemplary embodiment that designates continuous irradiation or pulse irradiation.

Then the operator designates still image capture or fluoroscopic imaging as an image capture mode at the operation panel 102. If fluoroscopic imaging is designated as the image capture mode, continuous irradiation or pulse irradiation is designated. An example of an instruction screen 190 for designating continuous irradiation or pulse irradiation, which is displayed at the display 100 in a case in which fluoroscopic imaging is designated, is illustrated in FIG. 6. In the instruction screen 190, a button 190A for designating continuous irradiation and a button 190B for designating pulse irradiation are provided.

If still image capture is designated as the image capture mode, the operator then designates exposure conditions such as a tube voltage, a tube current, an irradiation duration and the like at the operation panel 102 for when radiation X is irradiated. If fluoroscopic imaging is designated as the image capture mode, the operator designates exposure conditions such as a frame rate, a tube voltage, an irradiation amount to be irradiated and the like at the operation panel 102. The designated image capture mode and exposure conditions are transmitted to the radiation generator 34 and the electronic cassette 32.

Figure 7A:
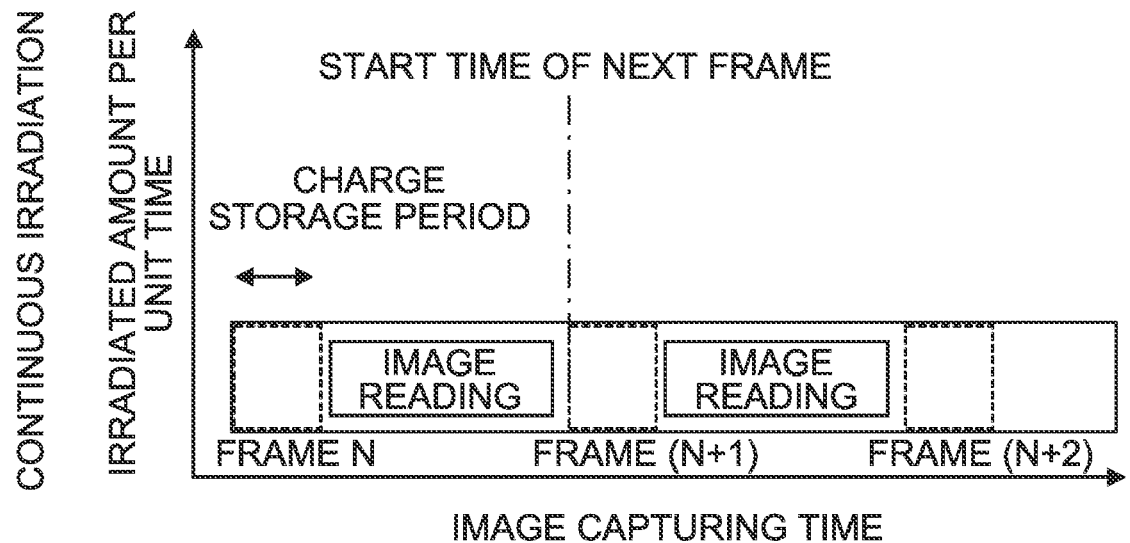
FIG. 7A and FIG. 7B are timing charts illustrating periods of irradiation of radiation, irradiation amounts of the radiation per unit time, and image detection timings for continuous irradiation and pulse irradiation relating to the exemplary embodiment.

As shown in FIG. 7A, in continuous irradiation, radiation is irradiated continuously, and radiation is irradiated also at the time of image read-out. Therefore, there is the need to keep the irradiated amount of radiation per unit time low and suppress the amount of radiation that the subject 48 is exposed to.

Figure 7B:
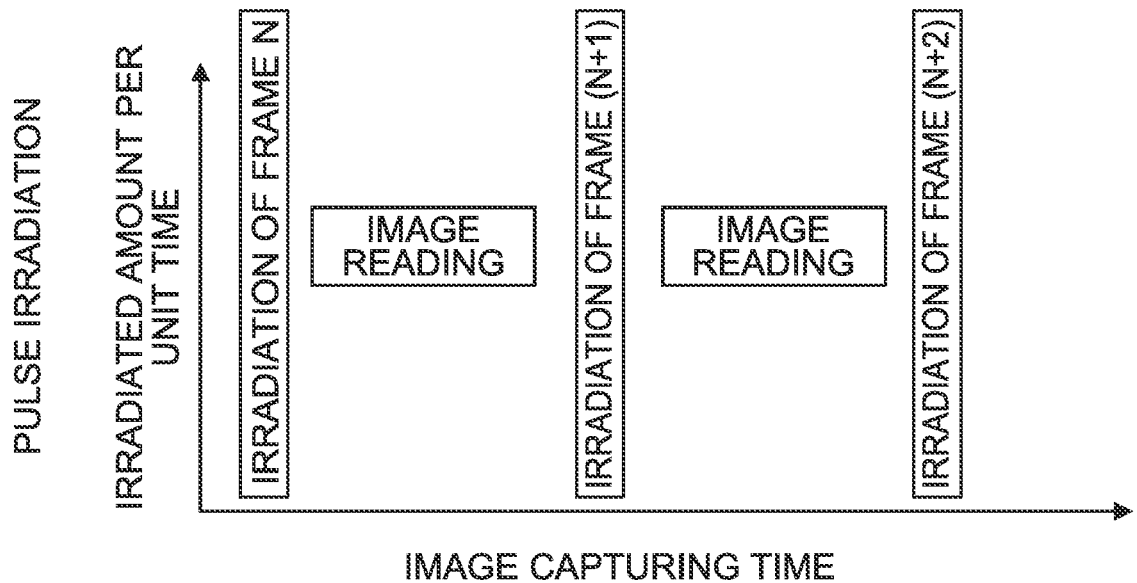

However, as illustrated in FIG. 7B, pulse irradiation has an advantage in that radiation may be irradiated only in periods required for image capture, amounts exposed onto the patient may be suppressed in comparison with continuous irradiation, and therefore an irradiation amount per unit time is raised. Moreover, because the duration of irradiation of the radiation is shortened, even if a portion moves, an image in which the movement is paused may be captured.

Therefore, in the present exemplary embodiment, in a case in which continuous irradiation of radiation is carried out, the ranges over which the tube voltage and the tube current can be designated from the operation panel 102 are limited so that the irradiated radiation amount per unit time is reduced as compared with a case in which pulse irradiation of radiation is carried out. The amount of radiation to which the subject is exposed at the time of continuous irradiation can thereby be suppressed.

When fluoroscopic imaging with pulse irradiation is to be performed, the console 42 transmits a synchronization signal with a period corresponding to the designated frame rate to the radiation generator 34 and the electronic cassette 32. The radiation generator 34 generates and emits radiation each time the synchronization signal is received, and the electronic cassette 32 performs image capture each time the synchronization signal is received.

Now, if radio communication is being performed between the electronic cassette 32 and the console 42 when fluoroscopic imaging with pulse irradiation is being carried out, delays and losses may occur in the synchronization signal that is transmitted by radio communication, and it may not be possible to reliably capture fluoroscopic images.

In contrast, depending on the content of an image capture request, it may not be preferable to perform fluoroscopic imaging with continuous irradiation. For example, if the subject 48 is a baby or a small child, the subject 48 may inadvertently move adversely during image capture. With pulse irradiation, images may shake and have to be recaptured.

Accordingly, in the present exemplary embodiment, in a case in which the electronic cassette 32 and the console 42 communicate by radio, fluoroscopic imaging with pulse irradiation is prohibited and in a case in which performing fluoroscopic imaging with continuous irradiation is not preferable based on the content of an image capture request, fluoroscopic imaging with pulse irradiation is maintained.

Figure 8:
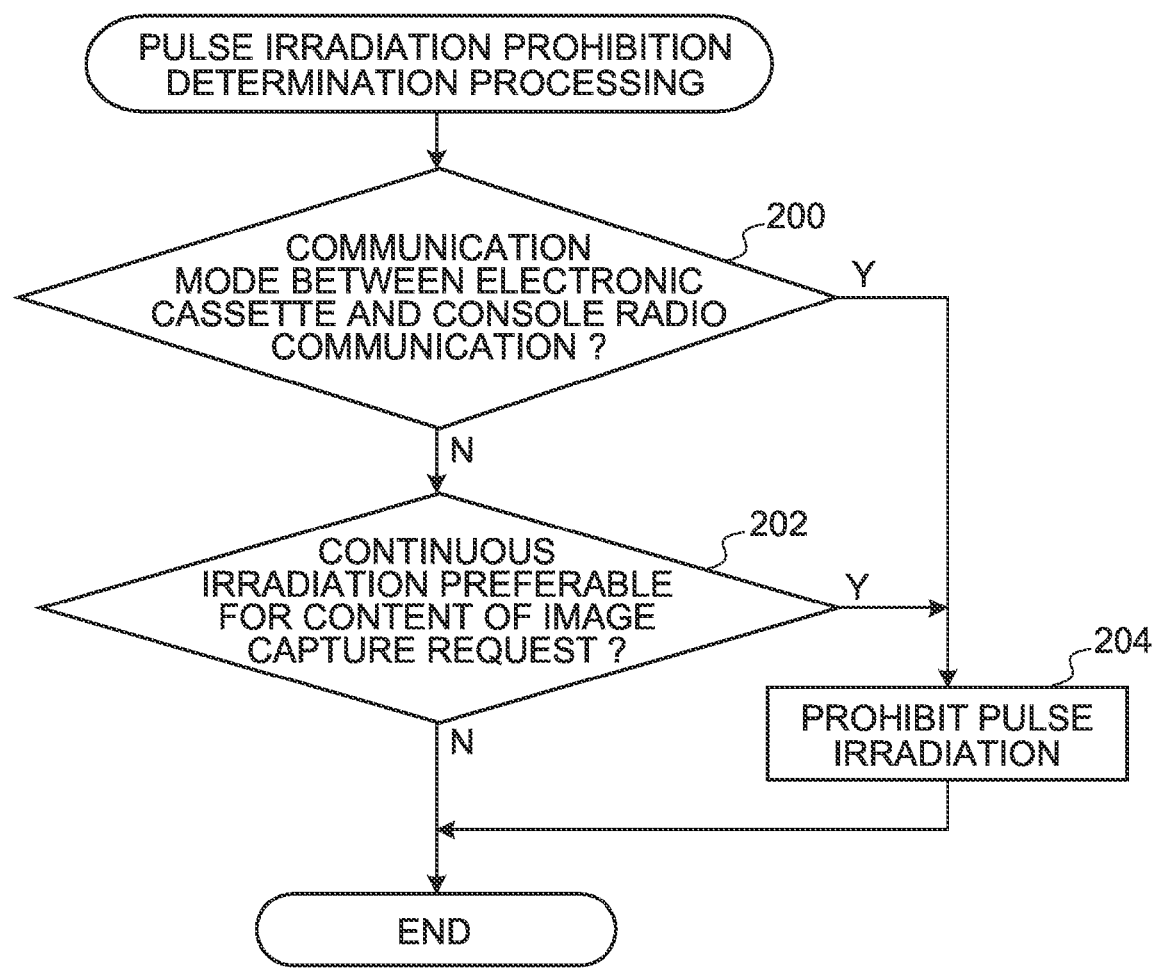
FIG. 8 is a flowchart illustrating a flow of a pulse irradiation prohibition determination processing program relating to the first exemplary embodiment.

FIG. 8 shows a flowchart illustrating a flow of a pulse irradiation prohibition determination processing program relating to the first exemplary embodiment that is executed by the CPU 104. This program is pre-memorized in a predetermined region of the HDD 110, and is executed in response to an instruction operation instructing fluoroscopic imaging being performed at the operation panel 102.

In step 200 of FIG. 8, it is determined whether or not a communication mode between the electronic cassette 32 and the console 42 is radio communication. If this determination is positive, the process proceeds to step 204, and if the determination is negative, the process proceeds to step 202.

In step 202, it is determined whether or not the content of the image capture request is content for which fluoroscopic imaging with continuous irradiation is preferable. If this determination is positive, the process proceeds to step 204, and if the determination is negative, the processing ends. For example, if an age of the subject 48 found from attribute data of the subject 48 is the age of a baby or a small child (for example, 0 to 6 years old), fluoroscopic imaging with continuous irradiation is inappropriate and the determination is negative.

In step 204, fluoroscopic imaging with pulse irradiation is prohibited, and the processing ends. In the present exemplary embodiment, the button 190B for designating pulse irradiation in the instruction screen 190 (FIG. 6) is disabled and pulse irradiation cannot be selected. Thus, fluoroscopic imaging with pulse irradiation is prohibited. If fluoroscopic imaging with pulse irradiation has been prohibited, operations may be performed with continuous operation while fluoroscopic imaging is designated as the image capture mode, without the instruction screen 190 being displayed.

Therefore, in a case in which the electronic cassette 32 and the console 42 communicate by radio in fluoroscopic imaging, and in a case in which performing fluoroscopic imaging with continuous irradiation is preferable based on the content of an image capture request, the fluoroscopic imaging is performed with continuous irradiation.

When the operator completes image capture preparation, the operator may perform an image capture start operation at the operation panel 102 of the console 42 that instructs the start of capturing.

In response to the image capture start operation being carried out at the operation panel 102, the console 42 starts the image capture operations illustrated in FIG. 9 to FIG. 11 as below, depending on which of still image capture, fluoroscopic imaging with continuous irradiation and fluoroscopic imaging with pulse irradiation has been designated.

Figure 9:
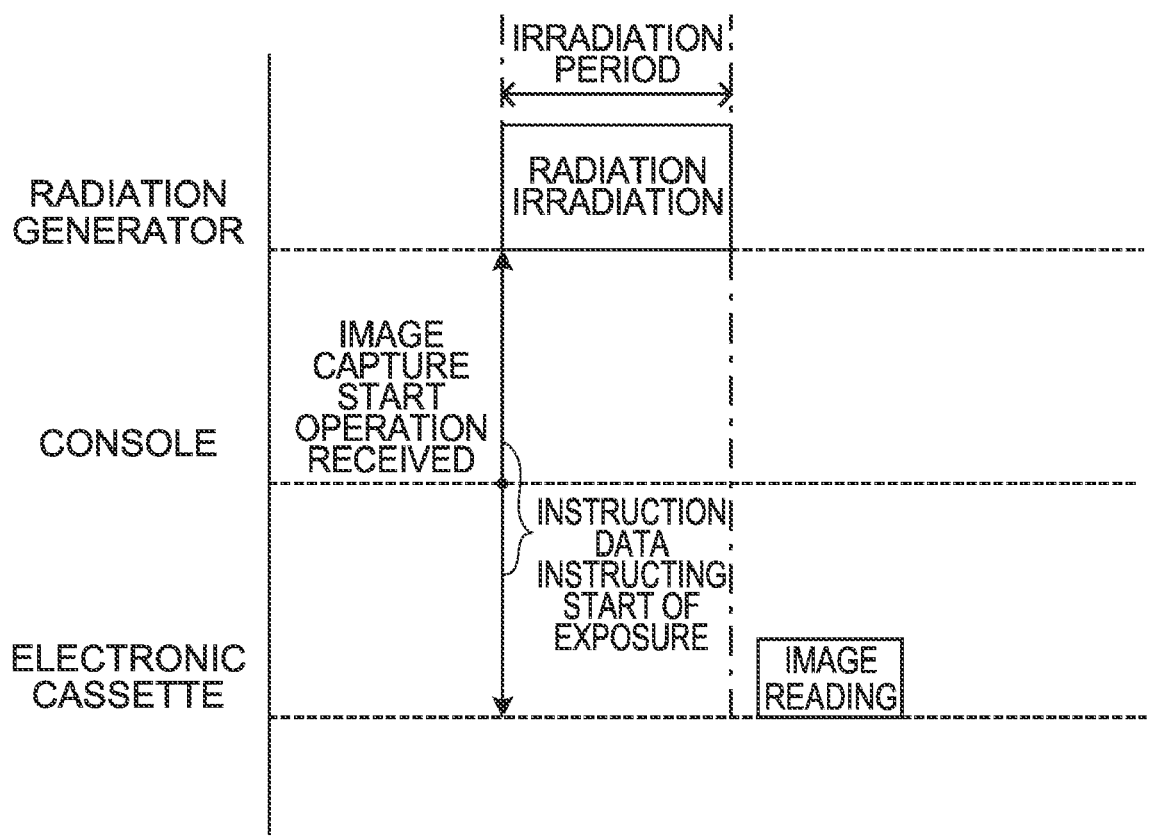
FIG. 9 is a timing chart illustrating a flow of capture operations relating to the exemplary embodiment in a case in which still image capture is instructed.

FIG. 9 shows a timing chart illustrating a flow of image capture operations in a case in which still image capture is instructed.

In response to the image capture start operation being carried out at the operation panel 102, the console 42 transmits instruction information (data) instructing the start of exposure to the radiation generator 34 and the electronic cassette 32.

In response to the reception of the instruction data instructing the start of exposure, the radiation generator 34 generates and emits radiation with a tube voltage, tube current and irradiation duration corresponding to the exposure conditions received from the console 42.

After receiving the instruction data instructing the start of exposure, the cassette controller 92 of the electronic cassette 32 controls the gate line driver 80 and, after the irradiation duration designated by the exposure conditions has passed, causes ON signals to be sequentially output in line units from the gate line driver 80 to the gate lines 76, and sequentially turns ON the TFTs 70 connected to the respective gate lines 76 in line units.

At the radiation detector 60, in response to the respective TFTs 70 being connected to the gate lines 76 are sequentially turned on in line units, the charges that have been stored in the storage capacitors 68 flow out to the data lines 78 as electronic signals, sequentially in line units. The electronic signals flowing out to the data lines 78 are converted to digital image data by the signal processor 82, are stored in the image memory 90, and are transmitted to the console 42.

The console 42 applies various kinds of corrective image processing such as shading correction and the like to the received image data, and stores the image-processed image data in the HDD 110. The image data that has been stored in the HDD 110 is displayed at the display 100 for checking of the captured radiographic image, and is also transferred to the RIS server 14 and saved to the database 14A. Hence, doctors may carry out interpretation, diagnostics and the like with the captured radiographic image.

Figure 10:
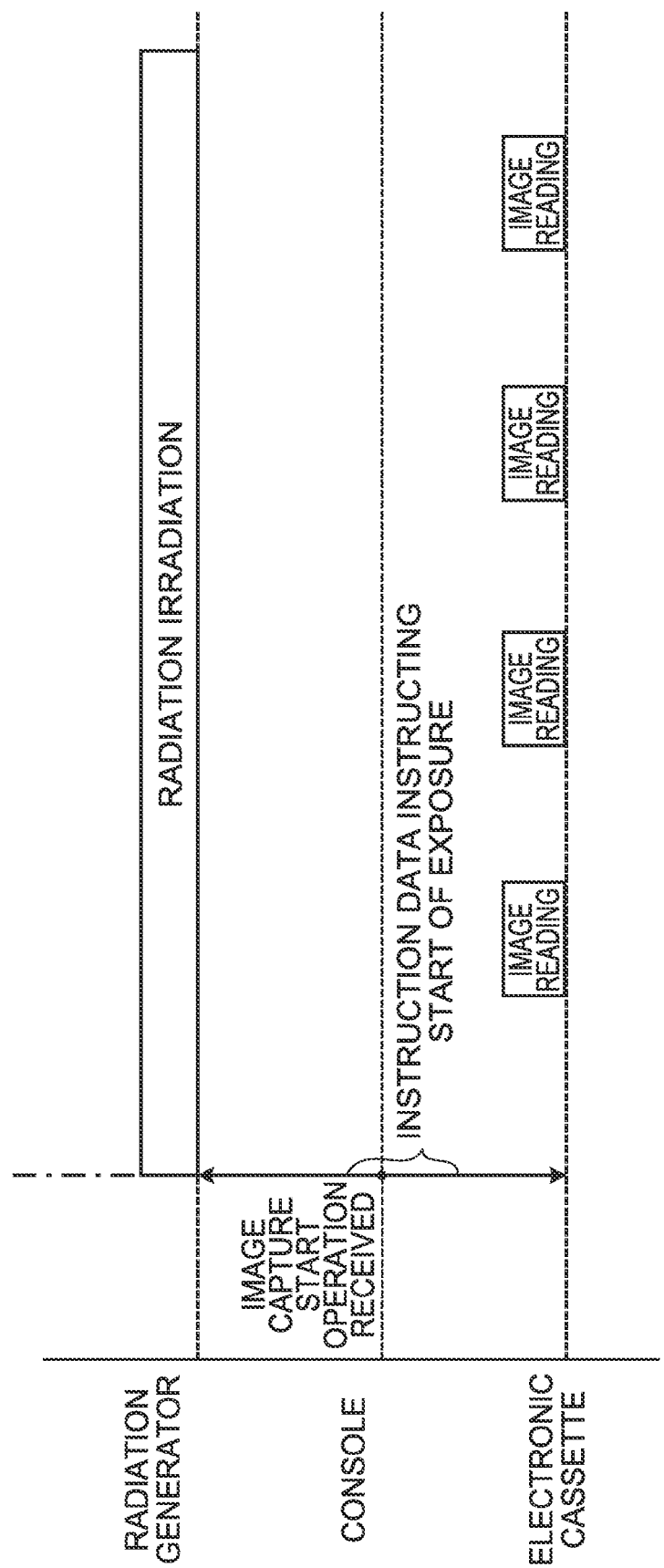
FIG. 10 is a timing chart illustrating a flow of capture operations relating to the exemplary embodiment in a case in which fluoroscopic imaging with continuous irradiation is instructed.

FIG. 10 shows a timing chart illustrating a flow of image capture operations in a case in which fluoroscopic imaging with continuous irradiation is instructed.

In response to the image capture start operation being carried out at the operation panel 102, the console 42 transmits instruction data instructing the start of exposure to the radiation generator 34 and the electronic cassette 32.

In response to a reception of the instruction data instructing the start of exposure, the radiation generator 34 starts the irradiation of radiation with a tube voltage and tube current corresponding to the exposure conditions received from the console 42.

In response to a reception of the instruction data instructing the start of exposure, the cassette controller 92 of the electronic cassette 32 controls the gate line driver 80 with a period corresponding to the designated frame rate, causes ON signals to be sequentially output in line units from the gate line driver 80 to the gate lines 76, sequentially turns ON the TFTs 70 connected to the respective gate lines 76 in line units, repeatedly reads the images, and reads out the images at the designated frame rate. The electronic signals flowing out to the data lines 78 of the radiation detector 60 are converted to digital image data by the signal processor 82, are stored in the image memory 90, and are transmitted to the console 42 by one image (frame) worth of data amount at a time. Similarly to the case of still image capture, the image data transmitted to the console 42 is subjected to various kinds of corrective image processing such as shading correction and the like by the console 42 and is stored in the HDD 110. The image data that has been stored in the HDD 110 is displayed at the display 100 for checking of the captured radiographic image, and is also transferred to the RIS server 14 and saved to the database 14A.

In response to an image capture end instruction being carried out at the operation panel 102, the console 42 transmits instruction data instructing the end of exposure to the radiation generator 34 and the electronic cassette 32. Hence, the radiation source 130 stops the irradiation of radiation and the electronic cassette 32 stops the reading of images.

Figure 11:
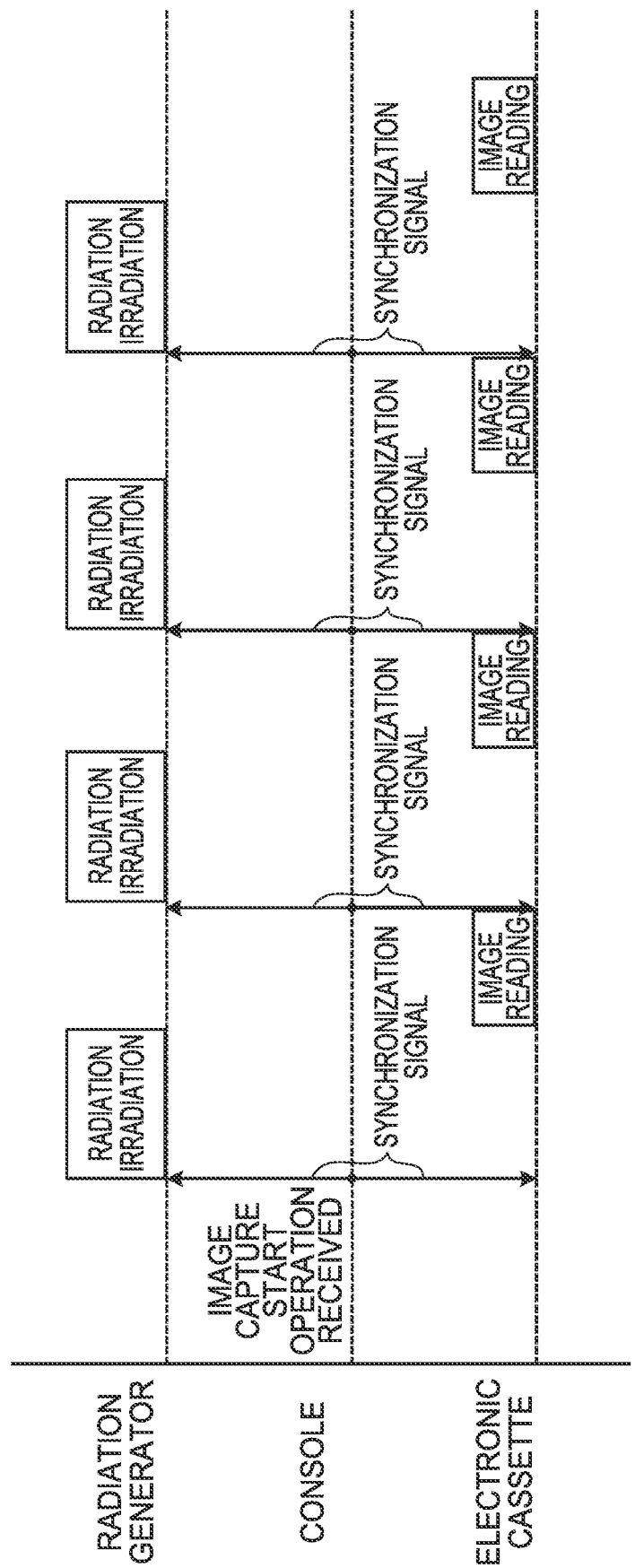
FIG. 11 is a timing chart illustrating a flow of capture operations relating to the exemplary embodiment in a case in which fluoroscopic imaging with pulse irradiation is instructed.

FIG. 11 is a timing chart illustrating a flow of image capture operations in a case in which fluoroscopic imaging with pulse irradiation is instructed.

The console 42 transmits a synchronization signal with a period corresponding to the designated frame rate to the radiation generator 34 and the electronic cassette 32.

Each time the radiation generator 34 receives the synchronization signal, the radiation generator 34 generates and emits radiation with a tube voltage, tube current and irradiation duration corresponding to the exposure conditions received from the console 42.

After receiving the synchronization signal, the cassette controller 92 of the electronic cassette 32 controls the gate line driver 80 and, after the irradiation duration designated by the exposure conditions has passed, causes ON signals to be sequentially output in line units from the gate line driver 80 to the gate lines 76, and sequentially turns ON the TFTs 70 connected to the respective gate lines 76 in line units and reads an image. The electronic signals flowing out to the data lines 78 of the radiation detector 60 are converted to digital image data by the signal processor 82, are stored in the image memory 90, and are transmitted to the console 42 by one image (frame) worth of data amount at a time. Similarly to the case of still image capture, the image data transmitted to the console 42 is subjected to various kinds of corrective image processing such as shading correction and the like by the console 42 and is stored in the HDD 110. The image data that has been stored in the HDD 110 is displayed at the display 100 for checking of the captured radiographic image, and is also transferred to the RIS server 14 and saved to the database 14A.

In response to the image capture end instruction being carried out at the operation panel 102, the console 42 transmits instruction data instructing the end of exposure to the radiation generator 34 and the electronic cassette 32. Hence, the radiation source 130 stops the irradiation of radiation and the electronic cassette 32 stops the reading of images.

In case of performing fluoroscopic imaging with continuous irradiation, the radiation amount per unit time that is irradiated is reduced compared to a case in which pulse irradiation is carried out. Therefore, in a case in which the cassette controller 92 carries out fluoroscopic imaging with continuous irradiation, at least one of the following may be implemented: a period of storage of charges in the pixels 74 is extended; the gain of the operational amplifiers 84A is increased; and image processing of treating plural adjacent pixels 74 as a single pixel.

Thus, even if fluoroscopic imaging is carried out with continuous irradiation and a radiation amount per unit time that is irradiated is reduced, excellent images may be obtained.

At the radiation generator, failures of radiographic image capture in which shake occurs because of some object touching or colliding against the radiation source 130 during capture may be prevented.

Accordingly, in the radiation generator 34 relating to the present exemplary embodiment, in order to prevent failures of radiographic image capture because of some object touching or colliding against the radiation source 130 during capture, accelerations in three axes (dimensions) are detected by an acceleration sensor 156 at intervals of a pre-specified period (intervals of 0.1 seconds in the present exemplary embodiment) and acceleration information (data) representing the detected accelerations in three dimensions is transmitted to the console 42.

At the console 42, in order to determine whether shake has occurred at the radiation source 130 during image capture, a shake threshold is pre-memorized in the HDD 110, and whether or not a shake has occurred is determined by comparison of the accelerations in three dimensions with the threshold. In the present exemplary embodiment, two of the shake thresholds are memorized (a first shake threshold and a second shake threshold). The first shake threshold is a threshold amount of a magnitude at which shake of the irradiation region of the radiation from the radiation generator 34 is small and image capture would not fail, and the second shake threshold is a shake amount with which the irradiation region of the radiation from the radiation generator 34 is significantly displaced and image capture would fail.

In response to a reception of the acceleration data at the console 42 from the radiation generator 34, the console 42 executes erroneous irradiation prevention processing.

Figure 12:
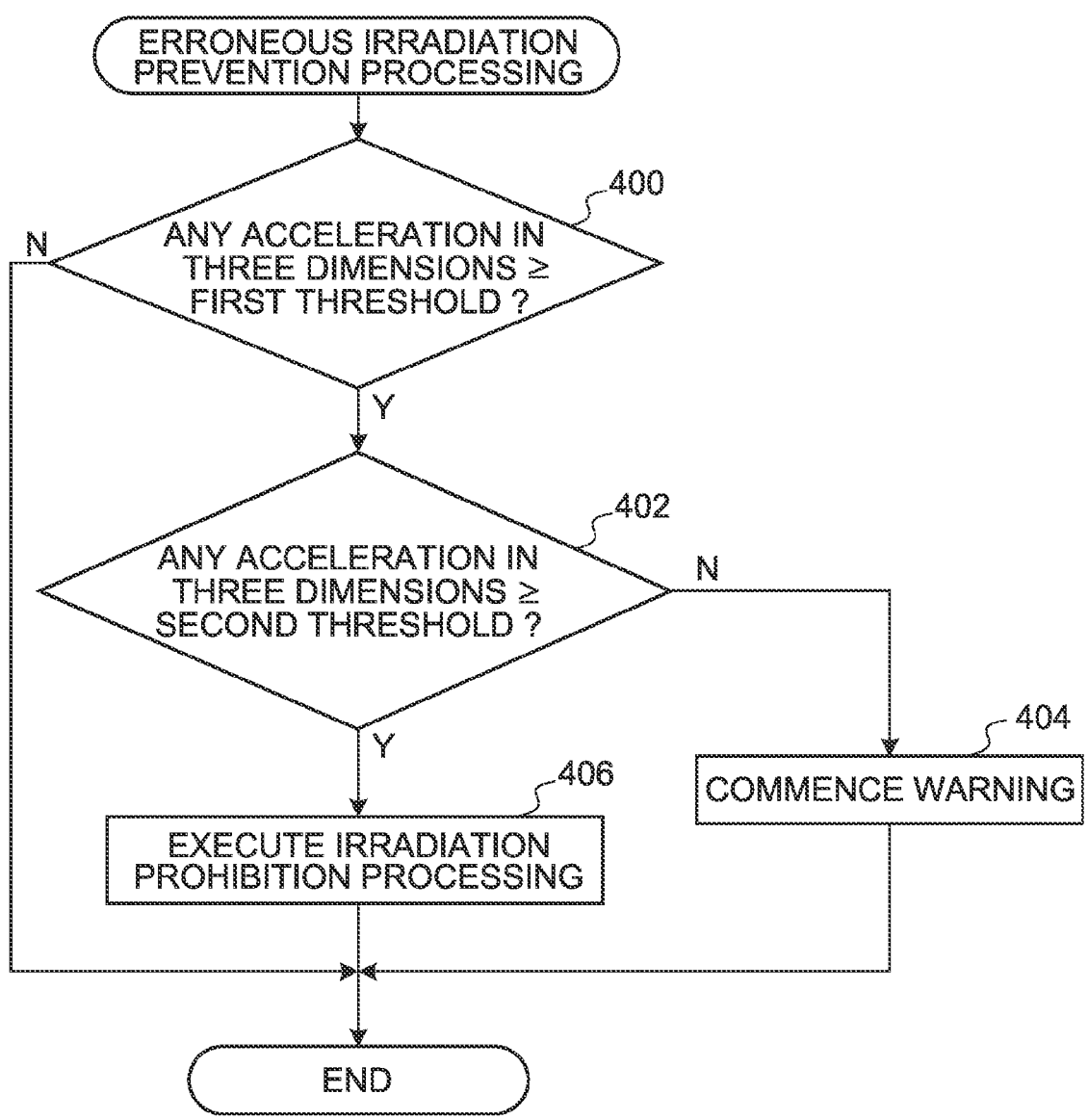
FIG. 12 is a flowchart illustrating a flow of an erroneous irradiation prevention processing program relating to the exemplary embodiment.

Operation of the console 42 executing the erroneous irradiation prevention processing is described with reference to FIG. 12. FIG. 12 is a flowchart illustrating a flow of an erroneous irradiation prevention processing program that is executed as interrupt processing by the CPU 104 of the console 42 at this time. This program is pre-memorized at a predetermined region of the ROM 106.

In step 400 of FIG. 12, it is determined whether or not any acceleration in three dimensions represented by the received acceleration data is at or above the first shake threshold. If this determination is negative, the present erroneous irradiation prevention processing program ends. If the determination is positive, the process proceeds to step 402.

In step 402, it is determined whether or not any acceleration in three dimensions represented by the received acceleration data is at or above the second shake threshold. If this determination is negative, the process proceeds to step 404. If the determination is positive, the process proceeds to step 406.

In step 404, a pre-specified warning is commenced, and then the present erroneous irradiation prevention processing program ends.

In the erroneous irradiation prevention processing program relating to the present exemplary embodiment, as the above-mentioned pre-specified warning, processing in which a warning screen that attracts attention is displayed by the display 100 of the console 42 is employed. However, embodiments are not to be limited to this. For example, in addition to a mode in which such information attracting attention is displayed by the display 100, any of other kinds of processing that can attract attention—such as processing in which a buzzer has been provided at the console 42 and this buzzer is caused to sound, processing in which a speaker has been provided at the console 42 and a message attracting attention is spoken by the speaker, processing in which a warning lamp has been provided at the console 42 and the warning lamp is lit or flashed, and the like—or a combination of these may be employed.

In step 406, pre-specified irradiation prohibition processing is executed, and then the present erroneous irradiation prevention processing program ends.

In the irradiation prohibition processing of the erroneous irradiation prevention processing program relating to the present exemplary embodiment, processing is employed in which a process that stops irradiation of the radiation X from the radiation source 130 is executed at the radiation generator 34, and a process is executed that causes a demonstrative screen showing that the irradiation of the radiation is prohibited to be displayed by the display 100 of the console 42, and then the execution of the above-described radiographic image capture processing program is forcibly ended. Furthermore, in the processing that stops irradiation of the radiation X of the erroneous irradiation prevention processing program relating to the present exemplary embodiment, processing is employed that transmits instruction data to the radiation generator 34 to forcibly cut a supply line of electric power for driving to the radiation source 130. However, exemplary embodiments are not to be limited to these. For example, processing that transmits instruction data to the radiation generator 34 that stops irradiation of the radiation X by the radiation source 130 or the like, or other processing capable of stopping irradiation of the radiation X by the radiation source 130 may be employed.

Thus, according to the present exemplary embodiment, if a contact or a collision or the like of some object against the radiation source 130 occurs and the radiation source 130 shakes, control is executed to prevent the irradiation of radiation from the radiation source. Therefore, failures of radiographic capturing due to contact with objects during capture, reductions in the quality of images obtained by capturing and the like may be prevented.

Second Exemplary Embodiment

The image capturing system 18 relating to the second exemplary embodiment is capable of radio communication between the console 42 and the radiation generator 34.

FIG. 13 shows a block diagram illustrating a configuration of principal elements of an electronic system of the image capturing system 18 relating to the second exemplary embodiment. Portions that are the same as in the image capturing system 18 of the first exemplary embodiment (see FIG. 4) are assigned the same reference numerals and will not be described.

The radiation generator 34 relating to the present exemplary embodiment is additionally provided with a radio communication unit 135 that sends and receives various kinds of information (data) by radio communication.

If the radiation generator 34 and console 42 relating to the present exemplary embodiment are connected by the communication cable 35, wired communication is performed and if the same are not connected by the communication cable 35, radio communication is performed.

Because the radiation generator 34 is capable of radio communication with the console 42, movements and arrangements may be implemented without being restricted by the communication cable 35.

In the present exemplary embodiment as well, if the radiation generator 34 and console 42 communicate by radio in a case in which performing fluoroscopic imaging with pulse irradiation, delays and/or losses may arise in a synchronization signal transmitted by radio communication, and it may not be possible to reliably capture fluoroscopic images.

Accordingly, in the present exemplary embodiment, in a case in which the radiation generator 34 and console 42 communicate by radio, fluoroscopic imaging with pulse irradiation is prohibited.

Figure 14:
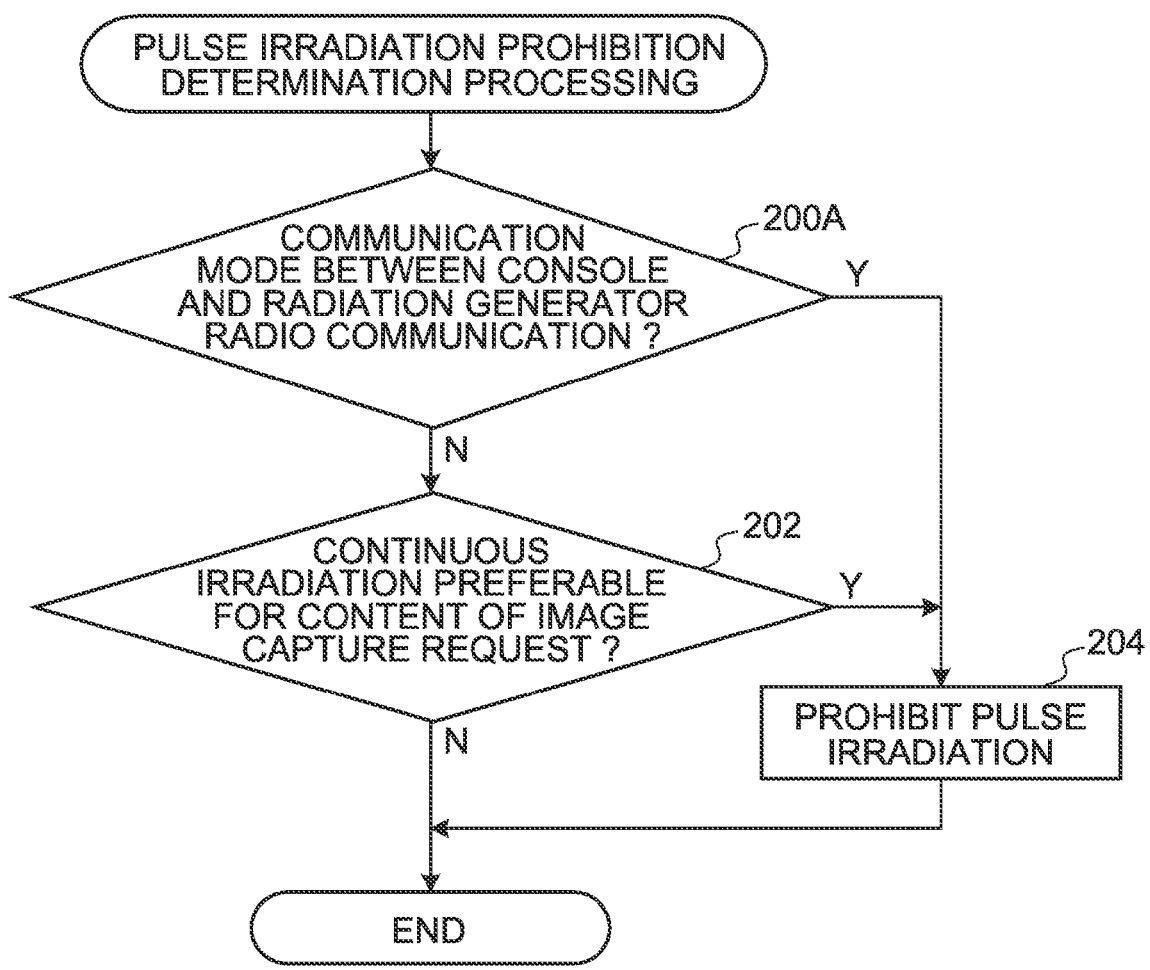
FIG. 14 is a flowchart illustrating a flow of a pulse irradiation prohibition determination processing program relating to the second exemplary embodiment.

FIG. 14 illustrates a flow of a pulse irradiation prohibition determination processing program relating to the present exemplary embodiment. Portions of the process that are the same as in the pulse irradiation prohibition determination processing program of the first exemplary embodiment (see FIG. 8) are assigned the same reference numerals and will not be described.

In step 200A, it is determined whether or not the communication mode between the radiation generator 34 and the console 42 is radio communication. If this determination is positive, the process proceeds to step 204, and if the determination is negative, the process proceeds to step 202.

Therefore, in a case in which the radiation generator 34 and the console 42 communicate by radio in fluoroscopic imaging, the fluoroscopic imaging is carried out with continuous irradiation.

Third Exemplary Embodiment

The image capturing system 18 relating to the third exemplary embodiment is not equipped with the console 42, but various kinds of instruction operation relating to imaging may be performed at the electronic cassette 32.

Figure 15:
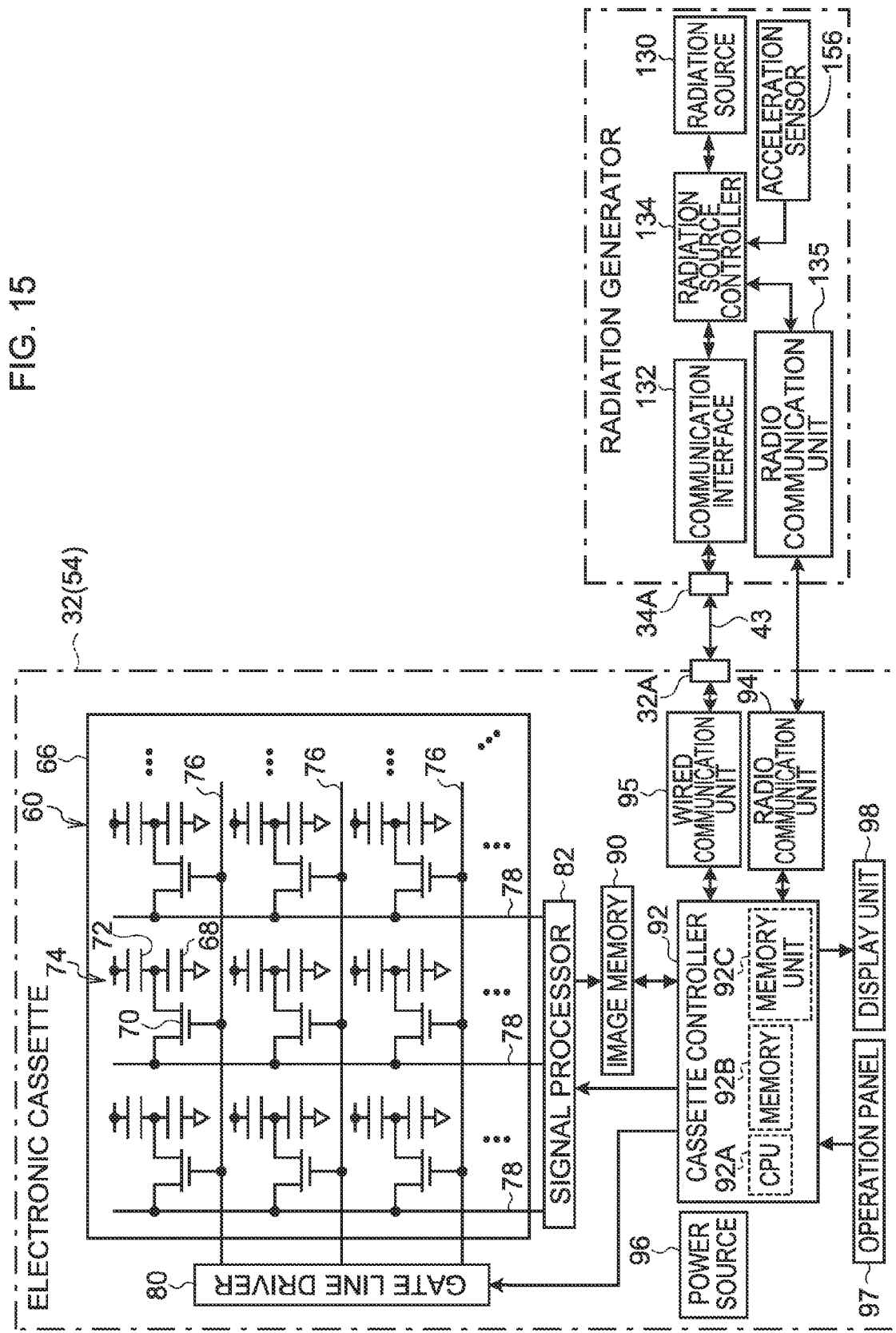
FIG. 15 is a block diagram illustrating a configuration of principal elements of an electronic system of an imaging system relating to a third exemplary embodiment.

FIG. 15 illustrates a configuration of principal elements of an electronic system of an imaging system relating to the third exemplary embodiment. Portions that are the same as in the image capturing system 18 of the first exemplary embodiment (see FIG. 4) are assigned the same reference numerals and descriptions thereof are omitted.

The radiation generator 34 relating to the present exemplary embodiment is provided with an operation panel 97 for various instruction operations relating to image capture by the electronic cassette 32 and with a display unit 98 for displaying various kinds of information. In the present exemplary embodiment, the operation panel 97 of the electronic cassette 32 may implement designation of the image capture mode, designation of continuous irradiation or pulse irradiation if fluoroscopic imaging is designated as the image capture mode, and designation of exposure conditions.

The connection terminal 32A and the connection terminal 34A may be connected by the communication cable 43. In a case in which the electronic cassette 32 and radiation generator 34 are interconnected by the communication cable 43, wired communication is performed, and in a case in which the same are not interconnected by the communication cable 43, radio communication is performed.

The electronic cassette 32 accesses the RIS server 14 to acquire the content of an image capture request and the attribute data of a patient to be captured from the RIS server 14, and displays the content of the image capture request and the attribute data of the patient at the display unit 98.

The operator disposes the electronic cassette 32 for the area to be captured, without connecting the communication cable 43 to the electronic cassette 32 and the radiation generator 34 if the electronic cassette 32 and the radiation generator 34 are to communicate by radio, or after interconnecting the electronic cassette 32 and the radiation generator 34 with the communication cable 43 if the electronic cassette 32 and the radiation generator 34 are to communicate by wire.

The operator designates still image capture or fluoroscopic imaging as the image capture mode at the operation panel 97, and if fluoroscopic imaging is designated as the image capture mode, designates one or other of continuous irradiation and pulse irradiation.

If fluoroscopic imaging with pulse irradiation is to be performed, the electronic cassette 32 transmits to the radiation generator 34 a synchronization signal with a period corresponding to the frame rate designated in the exposure conditions, reads images from the radiation detector 60 to match synchronization timings in accordance with the synchronization signal, and captures radiographic images.

If the electronic cassette 32 and the radiation generator 34 communicate by radio in performing fluoroscopic imaging with pulse irradiation, delays and/or losses may arise in the synchronization signal transmitted by radio communication, and it may not be possible to reliably capture fluoroscopic images.

Accordingly, in the present exemplary embodiment, in a case in which the radiation generator 34 and radiation generator 34 communicate by radio, fluoroscopic imaging with pulse irradiation is prohibited.

Figure 16:
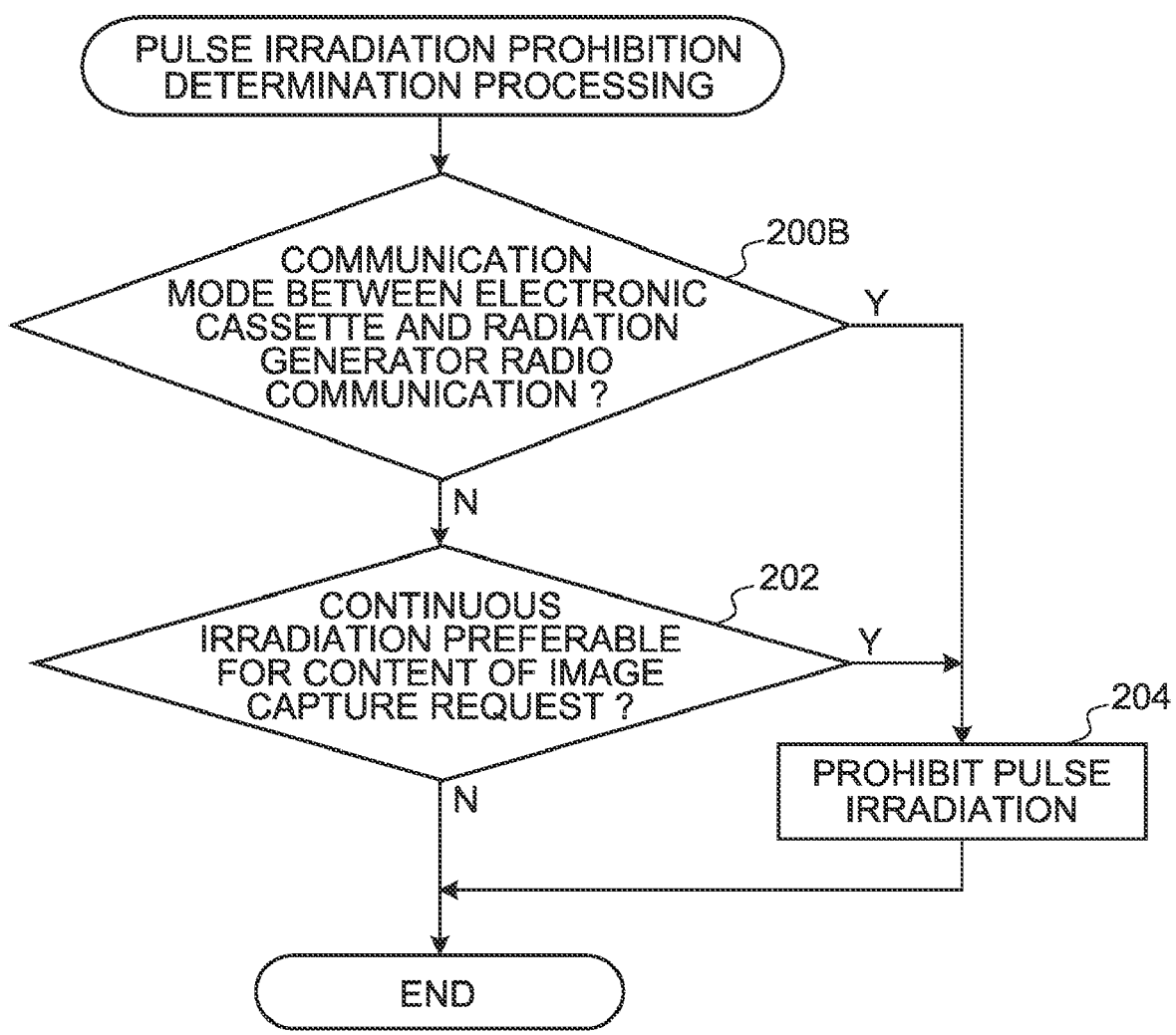
FIG. 16 is a flowchart illustrating a flow of a pulse irradiation prohibition determination processing program relating to the third exemplary embodiment.

FIG. 16 shows a flowchart illustrating a flow of a pulse irradiation prohibition determination processing program that is executed by the CPU 92A of the electronic cassette 32. This program is pre-memorized in a predetermined region of a ROM included in the memory 92B, and is executed in response to an instruction operation instructing fluoroscopic imaging is performed at the operation panel 97. Portions of the process that are the same as in the pulse irradiation prohibition determination processing program of the first exemplary embodiment (see FIG. 8) are assigned the same reference numerals and will not be described.

In step 200B of FIG. 16, it is determined whether or not the communication mode between the electronic cassette 32 and the radiation generator 34 is radio communication. If this determination is positive, the process proceeds to step 204, and if the determination is negative, the process proceeds to step 202.

Thus, in a case in which the electronic cassette 32 and the radiation generator 34 communicate by radio in fluoroscopic imaging, and in a case in which it is preferable to perform fluoroscopic imaging with continuous irradiation based on the content of an image capture request, the fluoroscopic imaging is performed with continuous irradiation.

Erroneous irradiation prevention processing may be executed at the image capturing system 18 relating to the third exemplary embodiment as well. In this case, at each cycle of a predetermined period during capturing, the radiation generator 34 detects accelerations in three dimensions with the acceleration sensor 156 and transmits acceleration data representing the detected accelerations in three dimensions to the electronic cassette 32.

In response to a reception of the acceleration data at the electronic cassette 32 from the radiation generator 34, the electronic cassette 32 may execute the erroneous irradiation prevention processing program with the CPU 92A.

For the pre-specified warning of the erroneous irradiation prevention processing program of the present exemplary embodiment, processing in which a warning screen that attracts attention is displayed by the display unit 98 of the electronic cassette 32 is employed. However, embodiments are not to be limited to this. For example, in addition to a mode in which such information attracting attention is displayed by the display unit 98, any of other kinds of processing that can attract attention—such as processing in which a buzzer has been provided at the electronic cassette 32 and this buzzer is caused to sound, processing in which a speaker has been provided at the electronic cassette 32 and a message attracting attention is spoken by the speaker, processing in which a warning lamp has been provided at the electronic cassette 32 and the warning lamp is lit or flashed, and the like—or a combination of these may be employed.

Further, for the irradiation prohibition processing of the erroneous irradiation prevention processing program in the present exemplary embodiment, processing is employed in which a process that stops irradiation of the radiation X from the radiation source 130 is executed at the radiation generator 34 and a process that causes an exhibition screen showing that the irradiation of the radiation is prohibited to be displayed by the display unit 98 of the electronic cassette 32 is executed, and then the execution of the above-described radiographic image capture processing program is forcibly ended. However, embodiments are not to be limited to this. As the processing that stops irradiation of the radiation X, processing that transmits instruction information to the radiation generator 34 that stops irradiation of the radiation X by the radiation source 130 or the like, or other processing capable of stopping irradiation of the radiation X by the radiation source 130 may be employed.

Hereabove, the present invention is described using exemplary embodiments, but the technical scope of the present invention is not to be limited to the scope described in the above exemplary embodiments. Numerous modifications and improvements may be applied to the above-described exemplary embodiments within a scope not departing from the spirit of the invention, and modes in which these exemplary embodiments and improvements are applied are to be included in the technical scope of the present invention.

Furthermore, the exemplary embodiments described above are not to limit the inventions relating to the claims, and means for achieving the invention are not necessarily to be limited to all of the combinations of features described in the exemplary embodiments. Various stages of the invention are included in the above-described exemplary embodiments, and various inventions may be derived by suitable combinations of the plural configuration elements that are disclosed. If some configuration element is omitted from the totality of configuration elements illustrated in an exemplary embodiment, as long as the effect thereof is provided, a configuration from which the some configuration element is omitted may be derived to serve as the invention.

In the exemplary embodiments described above, a case is described in which processing that prohibits the irradiation of the radiation X from the radiation source 130 if shake occurs is executed by the console 42. However, embodiments are not to be limited by this. For example, the processing may be executed by the radiation generator 34 itself. As an example of this case, a mode in which an erroneous irradiation prevention processing program (see FIG. 12) is executed by the radiation source controller 134 of the radiation generator 34 may be exemplified. Obviously, there is no need to perform processing for transmitting and receiving distance data in this case. This case also may realize the same effects as the above exemplary embodiments.

In the exemplary embodiments described above, a case is described in which an age range of babies and small children is memorized as unsuitable condition information, and if an age of the subject 48 that is found from attribute data of the subject 48 is an age of a baby or small child, it is determined that fluoroscopic imaging with the radiation being continuously irradiated is unsuitable. However, embodiments are not to be limited to this. Other conditions in which fluoroscopic imaging with the radiation being continuously irradiated is unsuitable may be memorized at the HDD 110 or the like as unsuitable condition information (data).

In the exemplary embodiments described above, a case in which a C arm is included as the radiation generator 34 is described. However, embodiments are not to be limited to this. For example, a moving radiation generator that does not have a C-arm, such as disclosed in Japanese Patent Application Laid-Open (JP-A) No. 2005-323673, may be used. In this case as well, the same effects as in the exemplary embodiments described above may be realized.

In the exemplary embodiments described above, a case is described in which a moving structure is employed as the radiation generator 34. However, embodiments are not to be limited to this. For example, a structure in which only the radiation source 130 of the radiographic image capturing room 44 is moved by a moving mechanism may be employed as the radiation generator. In this case, distances from other objects relative to the radiation source 130 and the moving mechanism are calculated and employed similarly to the above-described exemplary embodiments. In this case as well, the same effects may be realized as in the exemplary embodiments described above.

In the exemplary embodiments described above, a case is described in which the electronic cassette 32 is employed separately rather than being attached to the radiation generator 34. However, embodiments are not to be limited to this. For example, the electronic cassette 32 may be used in a state of being attached to the attachment structure 142 of the radiation generator 34. This case also may realize the same effects as in the exemplary embodiments described above.

In the exemplary embodiments described above, a case is described in which the acceleration sensor 156 is disposed in the vicinity of the radiation source 130. However, embodiments are not to be limited to this. For example, the acceleration sensor 156 may be disposed at the radiation source 130 itself. This case also may realize the same effects as in the exemplary embodiments described above.

A detection unit that detects shake is not to be limited to the acceleration sensor 156; an orientation sensor that detects changes in orientation may be employed and detect shake from changes in orientation. Alternatively, an encoder may be incorporated at a portion of a wheel 154 of the radiation generator 34 or a movable portion of the radiation generator 34 or the like, and shake may be detected from movement amounts of the wheel 154, the C arm 140 or the like using this encoder. Further still, a camera such as a visible light camera, an infrared camera or the like may be used. In this case, the camera need not necessarily be provided at the radiation generator 34. For example, the camera may be provided at a ceiling surface or floor surface of the radiographic image capturing room 44. As a method of calculating distances between the radiation generator 34 and other objects in this case, a technique may be employed in which the camera has been provided at the same position as the acceleration sensor 156, a region containing an area of the radiation generator 34 is continuously captured using the camera, and changes in images obtained by this capturing are detected.

Moreover, the configuration of the RIS 10 described in the above exemplary embodiments (see FIG. 1), the configurations of the radiographic image capturing room and the radiation generator 34 (see FIG. 2), the configuration of the electronic cassette 32 (see FIG. 3), and the configuration of the image capturing system 18 (see FIG. 4) are examples. Unnecessary portions may be removed, new portions may be added, and connection states and the like may be altered within a scope not departing from the spirit of the present invention.

The flows of the various programs described in the above exemplary embodiments (see FIG. 8 and FIG. 12) are examples. Unnecessary steps may be removed, new steps may be added, and sequences of processing may be rearranged within a scope not departing from the spirit of the present invention.

What is claimed is:

1. A radiographic image capturing system comprising:
a radiographic image capture device that is capable of wired communication via a communication cable and of wireless communication, and that is capable of fluoroscopic imaging in which radiographic images are successively captured at notified synchronization timings or at a predetermined frame rate;
a radiation irradiation device that irradiates radiation toward the radiographic image capture device during fluoroscopic imaging, with continuous irradiation or pulse irradiation; and
a control device that includes
a wireless communication unit that performs wireless communication with the radiographic image capture device,
a wired communication unit that performs wired communication with the radiographic image capture device via the communication cable, and
a controller that, in a case in which communication with the radiographic image capture device is performed by the wireless communication unit, prohibits fluoroscopic imaging with pulse irradiation in which the synchronization timings are notified to the radiographic image capture device and radiation is irradiated from the radiation irradiation device in pulses matching the notified synchronization timings.

2. The radiographic image capturing system according to claim 1, wherein
the control device further comprises a storage unit that memorizes unsuitable condition data representing a condition under which fluoroscopic imaging with continuous irradiation is unsuitable, and
the controller warns against or prohibits fluoroscopic imaging with continuous irradiation if the fluoroscopic imaging is to be carried out under the condition represented by the unsuitable condition data.

3. The radiographic image capturing system according to claim 1, wherein a radiation amount per unit time that is irradiated by the radiation irradiation device is smaller in the continuous irradiation than in the pulse irradiation.

4. The radiographic image capturing system according to claim 3, wherein the radiographic image capture device includes:
a radiographic detector in which a plurality of pixels that generate charges when radiation is irradiated thereon and store the charges are arranged in two dimensions, the radiographic detector outputting the charges stored in the pixels as electronic signals;
amplifiers that amplify the electronic signals output by the radiographic detector; and
an image capture device controller that, in case in which the continuous irradiation is performed, performs at least one of:
extending a storage period of the charges at the pixels to be longer than in the pulse irradiation;

increasing a gain amount of the amplifiers to be higher than in the pulse irradiation; or image processing that combines a plurality of adjacent pixels as a single pixel.

5. The radiographic image capturing system according to claim 1, further comprising a detector that detects shaking of the radiation irradiation device, wherein the controller initiates a warning if a shake amount of the radiation irradiation device detected by the detector during fluoroscopic imaging is at least a first shake threshold value, and stops irradiation of the radiation from the radiation irradiation device if the shake amount is at least a second shake threshold value, which is larger than the first shake threshold value.

6. The radiographic image capturing system according to claim 5, wherein the controller initiates the warning and stops the irradiation of the radiation if the detector detects shaking of the radiation detection device during fluoroscopic imaging with continuous irradiation.

7. A radiographic image capturing system comprising:

a radiation irradiation device that is capable of wired communication via a communication cable and of wireless communication, and that irradiates radiation during fluoroscopic imaging in which radiographic images are successively captured with continuous irradiation or with pulse irradiation synchronized with notified synchronization timings; and a control device that includes a wireless communication unit that performs wireless communication with the radiation irradiation device, a wired communication unit that performs wired communication with the radiation irradiation device via the communication cable, and a controller that, in a case in which communication with the radiation irradiation device is performed by the wireless communication unit, prohibits fluoroscopic imaging with pulse irradiation in which the synchronization timings are notified to the radiation irradiation device and radiation is irradiated from the radiation irradiation device in pulses matching the notified synchronization timings.

8. A radiographic image capturing system comprising:

a radiation irradiation device that is capable of wired communication via a communication cable and of wireless communication, and that irradiates radiation during fluoroscopic imaging in which radiographic images are successively captured, with continuous irradiation or with pulse irradiation synchronized with notified synchronization timings; and a control device that includes a wireless communication unit that performs wireless communication with the radiation irradiation device, a wired communication unit that performs wired communication with the radiation irradiation device via the communication cable, an image capture unit that performs image capture at the synchronization timings or at a predetermined frame rate, and a controller that, in case in which communication with the radiation irradiation device is performed by the wireless communication unit, prohibits fluoroscopic imaging with pulse irradiation in which the synchronization timings are notified to the radiation irradiation device and image capture is performed by the image capture unit in pulses matching the synchronization timings.

* * * * *